(12) United States Patent
Gross et al.

(10) Patent No.: US 11,905,195 B2
(45) Date of Patent: *Feb. 20, 2024

(54) METHOD OF FACILITATING OR INHIBITING GROWTH OF SPECIFIC MICROORGANISMS

(71) Applicant: Gross-Wen Technologies, Inc., Slate, IA (US)

(72) Inventors: Martin Gross, Boone, IA (US); Zhiyou Wen, Ames, IA (US); Xuefei Zhao, Ames, IA (US); Max Thomas Gangestad, Boone, IA (US)

(73) Assignee: Gross-Wen Te nologies, Inc., Slater, IA (US)

( * ) Notice: Subject to any disclaimer, the term of this patent is extended or adjusted under 35 U.S.C. 154(b) by 178 days.

This patent is subject to a terminal disclaimer.

(21) Appl. No.: 17/343,265

(22) Filed: Jun. 9, 2021

(65) Prior Publication Data
US 2021/0292201 A1 Sep. 23, 2021

Related U.S. Application Data

(63) Continuation-in-part of application No. 17/124,753, filed on Dec. 17, 2020, now Pat. No. 11,339,070,
(Continued)

(51) Int. Cl.
*C02F 3/32* (2023.01)
*A01G 33/00* (2006.01)
(Continued)

(52) U.S. Cl.
CPC .............. *C02F 3/322* (2013.01); *A01D 44/00* (2013.01); *A01G 33/00* (2013.01); *C02F 3/006* (2013.01);
(Continued)

(58) Field of Classification Search
CPC .. C02F 3/322; C02F 3/006; C02F 3/08; C02F 3/082; C02F 2101/105; C02F 2101/16;
(Continued)

(56) References Cited

U.S. PATENT DOCUMENTS 3,565,797 A 2/1971 Gresham
3,598,726 A 8/1971 Welch
(Continued)

FOREIGN PATENT DOCUMENTS

CN 103289887 A 9/2013
JP 2013-21976 A * 2/2013
(Continued)

OTHER PUBLICATIONS

Machine-generated English translation of JP 2013021976, generated on Mar. 31, 2023.*
(Continued)

*Primary Examiner* — Fred Prince
(74) *Attorney, Agent, or Firm* — Frost Brown Todd LLP; Vance V. VanDrake, III; Alexander J. Johnson

(57) ABSTRACT

A method of exposing microorganisms to a condition wherein the condition facilitates or inhibits growth of a specific species of microorganisms or a specific consortium of microorganisms. The condition may also stimulate microorganisms to uptake a pollutant from a fluid and/or release the pollutant. Furthermore, the microorganisms may also be harvested and used as a foodstuff for human and animal consumption.

21 Claims, 37 Drawing Sheets

Related U.S. Application Data which is a continuation of application No. 16/534,586, filed on Aug. 7, 2019, now Pat. No. 10,899,643.

(60) Provisional application No. 62/715,485, filed on Aug. 7, 2018.

(51) Int. Cl.

| | | |
|---|---|---|
| *C02F 3/08* | (2023.01) | |
| *A01D 44/00* | (2006.01) | |
| *C02F 3/00* | (2023.01) | |
| *C12N 1/12* | (2006.01) | |
| *C02F 101/10* | (2006.01) | |
| *C02F 101/16* | (2006.01) | |
| *C02F 101/30* | (2006.01) | |

(52) U.S. Cl.
CPC ............... *C02F 3/08* (2013.01); *C02F 3/082* (2013.01); *C12N 1/12* (2013.01); *C02F 2101/105* (2013.01); *C02F 2101/16* (2013.01); *C02F 2101/305* (2013.01); *C02F 2203/004* (2013.01); *C02F 2203/006* (2013.01); *Y02A 40/80* (2018.01); *Y02W 10/10* (2015.05); *Y02W 10/37* (2015.05)

(58) Field of Classification Search
CPC .......... C02F 2101/305; C02F 2203/004; C02F 2203/006; A01D 44/00; A01G 33/00; C12N 1/12; Y02A 40/80; Y02W 10/10; Y02W 10/37
USPC ....... 210/602, 614, 615, 616, 617, 400, 903, 210/906, 908, 911, 912, 913, 914
See application file for complete search history.

(56) References Cited

U.S. PATENT DOCUMENTS

| | | | |
|---|---|---|---|
| 4,324,068 A | 4/1982 | Anthony | |
| 4,554,390 A | 11/1985 | Curtain et al. | |
| 5,647,983 A | 7/1997 | Limcaco | |
| 5,778,823 A * | 7/1998 | Adey ..................... | A01K 61/00 119/215 |
| 6,158,386 A | 12/2000 | Limcaco | |
| 6,667,171 B2 | 12/2003 | Bayless et al. | |
| 6,794,184 B1 | 9/2004 | Mohr et al. | |
| 8,372,631 B2 | 2/2013 | Shepherd | |
| 8,377,687 B2 | 2/2013 | Shepherd | |
| 8,920,810 B2 | 12/2014 | Adey et al. | |
| 9,932,549 B2 | 4/2018 | Gross et al. | |
| 10,125,341 B2 | 11/2018 | Wen et al. | |
| 10,570,359 B2 | 2/2020 | Gross et al. | |
| 2008/0135474 A1 | 6/2008 | Limcaco | |
| 2009/0230040 A1 | 9/2009 | Limcaco | |
| 2010/0144017 A1 | 6/2010 | Shepherd | |
| 2010/0224574 A1 | 9/2010 | Youngs et al. | |
| 2010/0267122 A1 | 10/2010 | Chinnasamy et al. | |
| 2011/0070632 A1 | 3/2011 | Katoch et al. | |
| 2011/0217764 A1 | 9/2011 | Christenson et al. | |
| 2011/0258915 A1 | 10/2011 | Subhadra | |
| 2011/0263886 A1 | 10/2011 | Kale | |
| 2011/0283608 A1 | 11/2011 | Patel et al. | |
| 2011/0312062 A1 | 12/2011 | Nordvik et al. | |
| 2012/0018373 A1 | 1/2012 | Jones et al. | |
| 2012/0152832 A1 | 6/2012 | Johnson et al. | |
| 2012/0252105 A1 | 10/2012 | Ahrens et al. | |
| 2013/0149693 A1* | 6/2013 | Senaratne ................ | C12P 7/14 435/162 |
| 2013/0269244 A1 | 10/2013 | Jovine | |
| 2013/0319342 A1* | 12/2013 | Musser ................ | A01K 63/045 119/226 |
| 2014/0273171 A1 | 9/2014 | Gross et al. | |
| 2014/0273174 A1 | 9/2014 | Gross et al. | |
| 2016/0039693 A1 | 2/2016 | Kuehnle et al. | |
| 2016/0075989 A1 | 3/2016 | Carberry et al. | |
| 2016/0090317 A1 | 3/2016 | Ju et al. | |
| 2016/0130546 A1* | 5/2016 | Leimbach .............. | C12M 23/50 435/257.1 |
| 2017/0233272 A1 | 8/2017 | Chidambaran et al. | |
| 2017/0321181 A1 | 11/2017 | Hazlebeck et al. | |
| 2018/0171275 A1 | 6/2018 | Wen et al. | |
| 2018/0201887 A1 | 7/2018 | Gross et al. | |
| 2019/0248688 A1 | 8/2019 | Wen et al. | |
| 2020/0022384 A1 | 1/2020 | Gross et al. | |
| 2020/0024559 A1 | 1/2020 | Gross et al. | |
| 2020/0048122 A1 | 2/2020 | Gross et al. | |
| 2020/0123482 A1 | 4/2020 | Gross et al. | |
| 2020/0231477 A1 | 7/2020 | Wen et al. | |

FOREIGN PATENT DOCUMENTS

| | | |
|---|---|---|
| WO | 2010011320 A1 | 1/2010 |
| WO | 2010030953 A2 | 3/2010 |

OTHER PUBLICATIONS

Johnson et al., "Development of an attached microalgal growth system for biofuel production," Applied Microbiology and Biotechnology (2010), 85:525-534, Jul. 7, 2009.

Bitog et al., "Application of computational fluid dynamics for modeling and designing photobioreactors for microalgae production: A review," Computers and Electronics in Agriculture (2011), 76:131-147, Jan. 24, 2011.

Christenson et al. "Rotating Algal Biofilm Reactor and Spool Harvester for Wastewater Treatment with Biofuels By-Products," Biotechnology and Bioengineering, DOI 10.1002/bit.24451 (2012) Wiley Periodicals, Inc. Jan. 20, 2012.

International Search Report for International Application No. PCT/US2014/0299618, dated Aug. 21, 2014.

Written Opinion of the International Searching Authority for International Application No. PCT/US2014/029618, dated Aug. 21, 2014, 4 pages.

International Search Report for International Application No. PCT/US2020/014393 dated Mar. 25, 2020; 10 pages.

Peng, et al., Removal of total dissolved solids from wastewater using a revolving algal biofilm reactor, Water Environment Research, Nov. 12, 2019 [retrieved on Mar. 1, 2020]. Retrieved from the Internet<URL: https://onlinelibrary.wiley.com/doi/abs/10.1002/wer. 1273> Abstract.; 2 pages.

\* cited by examiner

Providing a microorganism growing apparatus 12 having a first reservoir 42 and a second reservoir 44

Filling the first reservoir 42 with a first fluid 58 that contains a pollutant 56

Controlling the first fluid 58 within the first reservoir 42 to have a first condition 64

Filling the second reservoir 44 with a second fluid 60

Controlling the second fluid 60 within the second reservoir 44 to have a second condition 66

Growing microorganisms 84

Providing a microorganism growing apparatus 12 having a first reservoir 42 and a second reservoir 44

Filling the first reservoir 42 with a first fluid 58 that contains a pollutant 56

Controlling the first fluid 58 within the first reservoir 42 to have a first condition 64

Filling the second reservoir 44 with a second fluid 60

Controlling the second fluid 60 within the second reservoir 44 to have a second condition 66

Growing microorganisms 84 using the microorganism growing apparatus 12 as the microorganisms 84 are exposed to the first fluid 58 within the first reservoir 42 wherein the microorganisms 84 are exposed to the first condition 64 and the microorganisms 84 uptake the pollutant 56 from the first fluid 58, then the microorganisms 84 are exposed to light 50 and carbon dioxide 48, and then the microorganisms 84 are exposed to the second fluid 60 within the second reservoir 44 wherein the microorganisms 84 are exposed to the second condition 66 and the microorganisms 84 are stimulated to release the pollutant 56 wherein the microorganisms 84 are algae 52 and the algae 52 is *Chlorella* algae 78

FIG. 28

Providing a microorganism growing apparatus 12 having a first reservoir 42 and a second reservoir 44

Filling the first reservoir 42 with a first fluid 58 that contains a pollutant 56

Controlling the first fluid 58 within the first reservoir 42 to have a first condition 64

Filling the second reservoir 44 with a second fluid 60

Controlling the second fluid 60 within the second reservoir 44 to have a second condition 66

Growing microorganisms 84 using the microorganism growing apparatus 12 as the microorganisms 84 are exposed to the first fluid 58 within the first reservoir 42 wherein the microorganisms 84 are exposed to the first condition 64 and the microorganisms 84 uptake the pollutant 56 from the first fluid 58, then the microorganisms 84 are exposed to light 50 and carbon dioxide 48, and then the microorganisms 84 are exposed to the second fluid 60 within the second reservoir 44 wherein the microorganisms 84 are exposed to the second condition 66 and the microorganisms 84 are stimulated to release the pollutant 56 wherein the microorganisms 84 are algae 52 and the algae 52 is *Spirulina* algae 80

FIG. 29

Providing a microorganism growing apparatus 12 having a first reservoir 42 and a second reservoir 44

Filling the first reservoir 42 with a first fluid 58 that contains a pollutant 56

Controlling the first fluid 58 within the first reservoir 42 to have a first condition 64

Filling the second reservoir 44 with a second fluid 60

Controlling the second fluid 60 within the second reservoir 44 to have a second condition 66

Growing microorganisms 84 using the microorganism growing apparatus 12 as the microorganisms 84 are exposed to the first fluid 58 within the first reservoir 42 wherein the microorganisms 84 are exposed to the first condition 64 and the microorganisms 84 uptake the pollutant 56 from the first fluid 58, then the microorganisms 84 are exposed to light 50 and carbon dioxide 48, then the microorganisms 84 are exposed to the second fluid 60 within the second reservoir 44 wherein the microorganisms 84 are exposed to the second condition 66 and the microorganisms 84 are stimulated to release the pollutant 56

Providing a third reservoir 46

Filling the third reservoir 46 with a third fluid 62

Controlling the third fluid 62 within the third reservoir 46 to have a third condition 68

Submerging a portion of the microorganisms 84 within the third fluid 62 of the third reservoir 46 thereby exposing this portion of the microorganisms 84 to the third condition 68

FIG. 30

Providing a microorganism growing apparatus 12 having a first reservoir 42 and a second reservoir 44

↓

Filling the first reservoir 42 with a first fluid 58 that contains a pollutant 56

↓

Controlling the first fluid 58 within the first reservoir 42 to have a first condition 64

↓

Filling the second reservoir 44 with a second fluid 60

↓

Controlling the second fluid 60 within the second reservoir 44 to have a second condition 66

↓

Growing microorganisms 84 using the microorganism growing apparatus 12 as the microorganisms 84 are submerged within the first fluid 58 held within the first reservoir 42 exposing the microorganisms 84 to the first condition 64 wherein the microorganisms 84 uptake the pollutant 56 from the first fluid 58 held within the first reservoir 42

↓

Moving the microorganisms 84 such that it is exposed to carbon dioxide 48 and light 50

↓

Following the uptake of the pollutant 56, moving the microorganisms 84 such that it is submerged within the second fluid 60 held within the second reservoir 44 exposing the microorganisms 84 to the second condition 66 and stimulating the microorganisms 84 to release the pollutant 56

FIG. 31

Providing an algae biofilm growing apparatus 12 having a first reservoir 42 and a second reservoir 44

Filling the first reservoir 42 with a first fluid 58 that contains a pollutant 56

Controlling the first fluid 58 within the first reservoir 42 to have a first condition 64

Filling the second reservoir 44 with a second fluid 60

Controlling the second fluid 60 within the second reservoir 44 to have a second condition 66

Growing microorganisms 84 using the microorganism growing apparatus 12 as the microorganisms 84 are submerged within the first fluid 58 held within the first reservoir 42 exposing the microorganisms 84 to the first condition 64 wherein the microorganisms 84 uptake the pollutant 56 from the first fluid 58 held within the first reservoir 42

Moving the microorganisms 84 such that it is exposed to carbon dioxide 48 and light 50

Following the uptake of the pollutant 56, moving the microorganisms 84 such that it is submerged within the second fluid 60 held within the second reservoir 44 exposing the microorganisms 84 to the second condition 66 and stimulating the microorganisms 84 to release the pollutant 56

Providing a third reservoir 46

Filling the third reservoir 46 with a third fluid 62

Controlling the third fluid 62 within the third reservoir 46 to have a third condition 68

Submerging a portion of the microorganisms 84 within the third fluid 62 of the third reservoir 46 thereby exposing this portion of the microorganisms 84 to the third condition 68

FIG. 32

Providing a microorganism growing apparatus 12 having a first reservoir 42, a second reservoir 44, and at least one moving belt 36

Filling the first reservoir 42 with a first fluid 58 that has a high concentration of the pollutant 56

Controlling the first fluid 58 within the first reservoir 42 to have a first condition 64

Filling the second reservoir 44 with a second fluid 60

Controlling the second fluid 60 within the second reservoir 44 to have a second condition 66

Moving the at least one belt 36 between a first submerged position 70, wherein a portion of the at least one belt 36 is submerged within the first fluid 58 held within the first reservoir 42, and an exposed position 76, wherein a portion of the at least one belt 36 is not submerged within the first fluid 58 held within the first reservoir 42

Exposing the portion of the at least one belt 36 in the exposed position 76 to air 48 and light 50

Growing microorganisms 84 on the at least one belt 36 as the at least one belt 36 moves through the microorganism growing apparatus 12, wherein the microorganisms 84 cons Providing a microorganism growing apparatus 12 having a first reservoir 42, a second reservoir 44, and at least one moving belt 36

↓

Filling the first reservoir 42 with a first fluid 58 that has a high concentration of the pollutant 56

↓

Controlling the first fluid 58 within the first reservoir 42 to have a first condition 64

↓

Filling the second reservoir 44 with a second fluid 60

↓

Controlling the second fluid 60 within the second reservoir 44 to have a second condition 66

↓

Moving the at least one belt 36 between a first submerged position 70, wherein a portion of the at least one belt 36 is submerged within the first fluid 58 held within the first reservoir 42, and an exposed position 76, wherein a portion of the at least one belt 36 is not submerged within the first fluid 58 held within the first reservoir 42

↓

Exposing the portion of the at least one belt 36 in the exposed position 76 to air 48 and light 50

↓

Growing microorganisms 84 on the at least one belt 36 as the at least one belt 36 moves through the microorganism growing apparatus 12, wherein the microorganisms 84 consume the pollutant 56 from the first fluid 58 held within the first reservoir 42 during the growing process

↓

Submerging a portion of the at least one belt 36 within the second fluid 60 of the second reservoir 44 thereby exposing this portion of the at least one belt 36 to the second condition 66 thereby stimulating the microorganisms 84 contained on this portion of the belt 36 to release the pollutant 56

↓

Providing a third reservoir 46

↓

Filling the third reservoir 46 with a third fluid 62

↓

Controlling the third fluid 62 within the third reservoir 46 to have a third condition 68

↓

Submerging a portion of the microorganisms 84 within the third fluid 62 of the third reservoir 46 thereby exposing this portion of the microorganisms 84 to the third condition 68

FIG. 34

Providing a microorganism growing apparatus 12 having a first reservoir 42 and a second reservoir 44

Filling the first reservoir 42 with a first fluid 58 that contains a pollutant 56

Controlling the first fluid 58 within the first reservoir 42 to have a first condition 64

Allowing the second reservoir 44 to be dry/empty by not filling the second reservoir 44 with a fluid or by draining the second reservoir 44 of the fluid contained therein

Controlling the second reservoir 44 to have a second condition 66

Growing microorganisms 84 using the microorganism growing apparatus 12

Exposing the microorganisms 84 to the first fluid 58 within the first reservoir 42 wherein the microorganisms 84 are exposed to the first condition 64 and the microorganisms 84 uptake the pollutant 56 from the first fluid 58

Exposing the microorganisms 84 to light 50 and air 48; and exposing the microorganisms 84 to the second reservoir 44 wherein the microorganisms 84 are exposed to the second condition 66 and the microorganisms 84 are stimulated to release the pollutant 56

FIG. 35

METHOD OF FACILITATING OR INHIBITING GROWTH OF SPECIFIC MICROORGANISMS

CROSS REFERENCE TO RELATED APPLICATIONS

This patent application is a continuation-in-part of U.S. patent application Ser. No. 17/124,753, filed Dec. 17, 2020, which is a continuation of U.S. patent application Ser. No. 16/534,586, filed on Aug. 7, 2019, now U.S. Pat. No. 10,899,643, issued Jan. 26, 2021, which claims priority to U.S. Provisional Patent Application No. 62/715,485, filed on Aug. 7, 2018, and also claims priority to U.S. Provisional Patent Application No. 62/981,247, filed Feb. 25, 2020, each of which is hereby incorporated herein by reference in its entirety.

FIELD OF THE DISCLOSURE

This disclosure relates generally to systems and methods of facilitating or inhibiting growth of specific microorganisms that are used to remove a pollutant from a fluid.

BACKGROUND OF THE DISCLOSURE

There is a rising demand for improvements in wastewater treatment technology due to the decreasing availability of freshwater resources and requirements for higher quality water treatment processes across many industrial sectors. In nature phosphorous is one of the main limiting factors for algal biomass production. Thus, the efficient phosphorous removal from wastewater is vital to reduce the amount of pollutants from entering aqueous environments and thereby preventing algal bloom and eutrophication of water. On the other hand, the increased cost of essential plant nutrients requires a shift towards resource recovery.

The treatment of wastewaters is a major problem today. Currently, municipal and industrial treatment facilities do not have an effective technology for reducing pollutants in their discharged effluents, especially phosphorous. Different states have implemented or are currently implementing various phosphorous discharge limits for municipal and industrial wastewater effluents in compliance with the US EPA National Nutrient Strategy (US EPA, 2008a).

Existing technologies are available for pollutant removal from municipal and industrial wastewaters. However, those technologies are not cost-effective or environmentally friendly. For example, the chemical-based method for pollutant removal is expensive due to the large amount of chemicals (e.g., aluminum and magnesium salts) used. Additionally, the chemical removal of pollutants from wastewaters will result in metal-containing sludge which results in a disposal problem.

As one example, phosphorous is a pollutant that is extremely difficult to remove from wastewaters. One method of phosphorous removal is to use bacteria called polyphosphate-accumulating organisms (PAO) through an enhanced biological phosphorus removal (EBPR) process. In the EBPR process, the first step is anaerobic fermentation in which PAOs assimilate organic compounds in wastewater (such as volatile fatty acids) into storage products while obtaining energy by releasing phosphorous from the stored polyphosphates. In the second aerobic fermentation stage, PAOs oxidize the stored products to provide energy while accumulating large quantities of polyphosphate within their cells. The phosphorus fraction of the biomass in EBPR can be as high as 5-7%. The phosphorus-rich biomass can be separated from the treated water, thus removing the phosphorus from the wastewater. While EBPR process can effectively remove phosphorous from wastewater, the process has several disadvantages such as undesirable high phosphorous strength in effluent, a requirement of careful operation and monitoring of the system, recycling a large amount of wastewater within the system, and high energy use.

Some emerging technologies such as Bardenpho are also being implemented at wastewater treatment plants. In the Bardenpho process, a series of anaerobic-anoxic-aerobic are implemented before the conventional activated sludge process. This process, however, requires extra space and tanks for implementing the sequential process, and operation of the sequential tanks with different oxygenation levels is also complicated.

Furthermore, algal wastewater treatment has not been feasible in the past due to a low pollutant removal rate and the massive footprint required in order to grow algae in traditional systems. Therefore, there is a need for a process that can quickly, efficiently, and cost effectively remove a pollutant from a fluid.

BRIEF SUMMARY OF THE DISCLOSURE

For the reasons stated above, and for other reasons stated below which will become apparent to those skilled in the art upon reading and understanding the specification, there is a need in the art for an improved method of removing a pollutant from a fluid.

Thus it is a primary object of the disclosure to provide a method of using microorganisms to remove a pollutant from a fluid that is efficient.

Yet another object of the disclosure is to provide a method of using microorganisms to remove a pollutant from a fluid that is simple in design.

Another object of the disclosure is to provide a method of using microorganisms to remove a pollutant from a fluid that is inexpensive.

Yet another object of the disclosure is to provide a method of using microorganisms to remove a pollutant from a fluid, harvesting the microorganisms, and using the microorganisms as a foodstuff for human consumption.

Another object of the disclosure is to provide a method of using microorganisms to remove a pollutant from a fluid, harvesting the microorganisms, and using the microorganisms as a foodstuff for animal consumption.

Yet another object of the disclosure is to provide a method of using microorganisms to remove a pollutant from a fluid that is capable of meeting current pollutant discharge limits.

Another object of the disclosure is to provide a method of using microorganisms to remove a pollutant from a fluid that has a smaller footprint than other biological systems.

Yet another object of the disclosure is to provide a method of using microorganisms to efficiently and effectively remove a pollutant from effluent.

Another object of the disclosure is to provide a method of using microorganisms to remove a pollutant from a fluid that has a high pollutant removal rate.

Yet another object of the disclosure is to provide a method of using microorganisms to remove a pollutant from a fluid, harvesting the microorganisms, and using the microorganisms as a fertilizer.

Another object of the disclosure is to provide a method of using microorganisms to remove a pollutant from a fluid, harvesting the microorganisms, and using the microorganisms as a bioplastic.

Yet another object of the disclosure is to provide a method of using microorganisms to remove a pollutant from a fluid, harvesting the microorganisms, and using the microorganisms as a biofuel.

Another object of the disclosure is to provide a method of exposing microorganisms to a condition wherein the condition facilitates growth of one or more specific microorganisms that will efficiently remove pollutants from a fluid.

Yet another object of the disclosure is to provide a method of exposing microorganisms to a condition, wherein the condition inhibits growth of one or more specific microorganisms that will facilitate efficient removal of pollutants from a fluid.

These and other objects, features, or advantages of the present disclosure will become apparent from the specification and claims.

The disclosure relates to a method of using microorganisms, including, but not limited to, bacteria, fungi, and/or algae, to remove a pollutant from a fluid. Furthermore, the disclosure relates to a method of using microorganisms, including, but not limited to, bacteria, fungi, and/or algae, to remove a pollutant from a fluid utilizing a microorganism growing apparatus. Furthermore, the disclosure relates to a method of using microorganisms to remove a pollutant from a fluid utilizing a microorganism growing apparatus wherein the microorganisms are exposed to a first fluid containing a pollutant wherein the microorganisms are exposed to a first condition, exposing the microorganisms to light and air (or to a $CO_2$-rich gaseous phase or an $O_2$-rich gaseous phase, among other compositions), and then exposing the microorganisms to a second fluid wherein the microorganisms are exposed to a second condition and the microorganisms are stimulated to release the pollutant. Additionally, the disclosure relates to a method of exposing microorganisms to a condition wherein the condition facilitates or inhibits growth of a specific microorganism.

BRIEF DESCRIPTION OF THE DRAWINGS

The present disclosure will be more readily understood from a detailed description of some example embodiments taken in conjunction with the following figures:

FIG. 27 depicts a flow chart illustrating a system which utilizes a microorganism growing apparatus to remove a pollutant from a fluid according to one embodiment;

FIG. 28 depicts a flow chart illustrating a system which utilizes a microorganism growing apparatus to remove a pollutant from a fluid according to an alternate embodiment;

FIG. 29 depicts a flow chart illustrating a system which utilizes a microorganism growing apparatus to remove a pollutant from a fluid according to an alternate embodiment;

FIG. 30 depicts a flow chart illustrating a system which utilizes a microorganism growing apparatus to remove a pollutant from a fluid according to an alternate embodiment;

FIG. 31 depicts a flow chart illustrating a system which utilizes a microorganism growing apparatus to remove a pollutant from a fluid according to an alternate embodiment;

FIG. 32 depicts a flow chart illustrating a system which utilizes a microorganism growing apparatus to remove a pollutant from a fluid according to an alternate embodiment;

FIG. 33 depicts a flow chart illustrating a system which utilizes a microorganism growing apparatus to remove a pollutant from a fluid according to an alternate embodiment;

FIG. 34 depicts a flow chart illustrating a system which utilizes a microorganism growing apparatus to remove a pollutant from a fluid according to an alternate embodiment;

FIG. 35 depicts a flow chart illustrating a system which utilizes a microorganism growing apparatus to remove a pollutant from a fluid according to an alternate embodiment;

DETAILED DESCRIPTION

Figure 1:
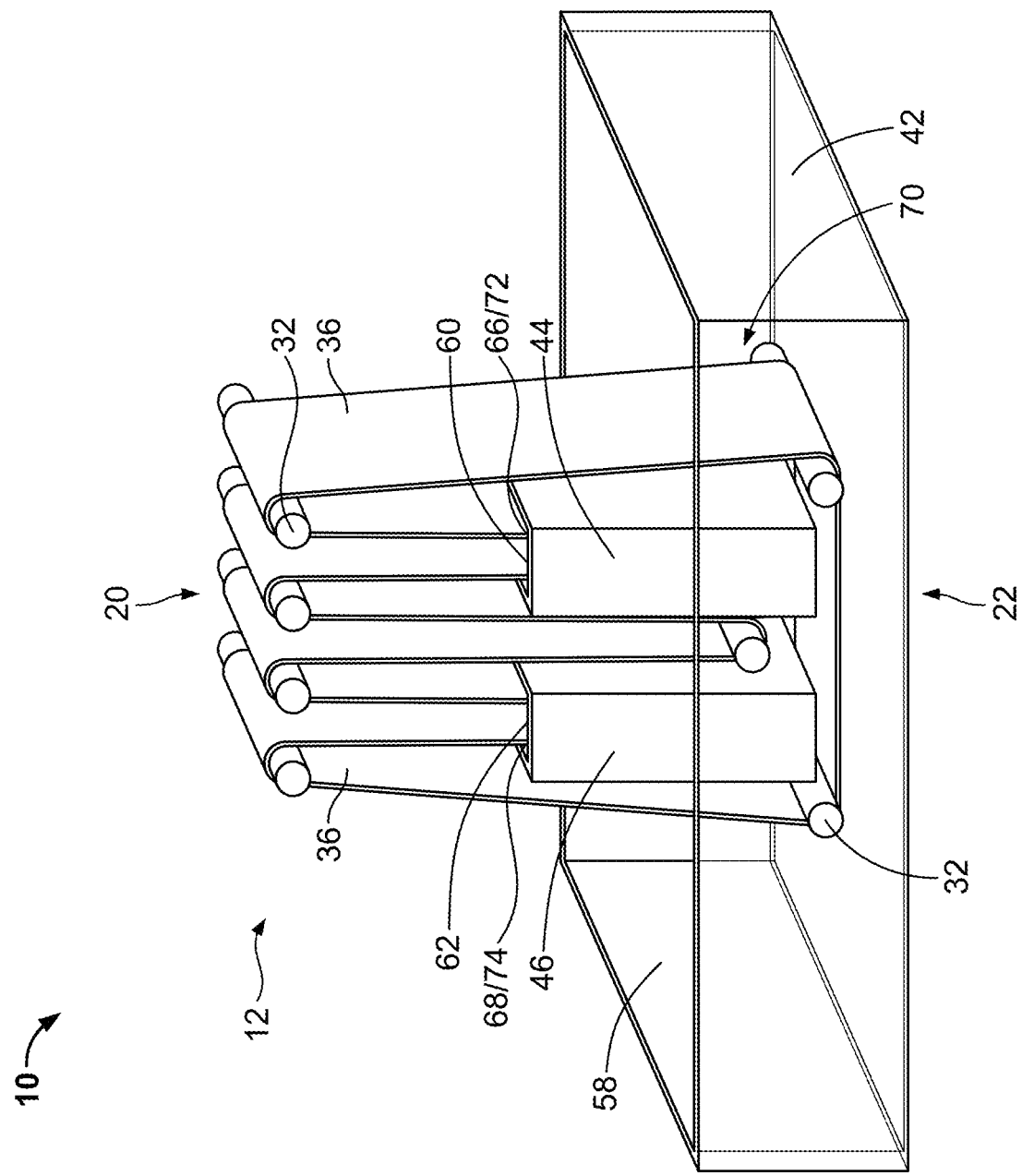
FIG. 1 depicts a perspective view of a system which utilizes microorganisms for removing a pollutant from a fluid.
Figure 2:
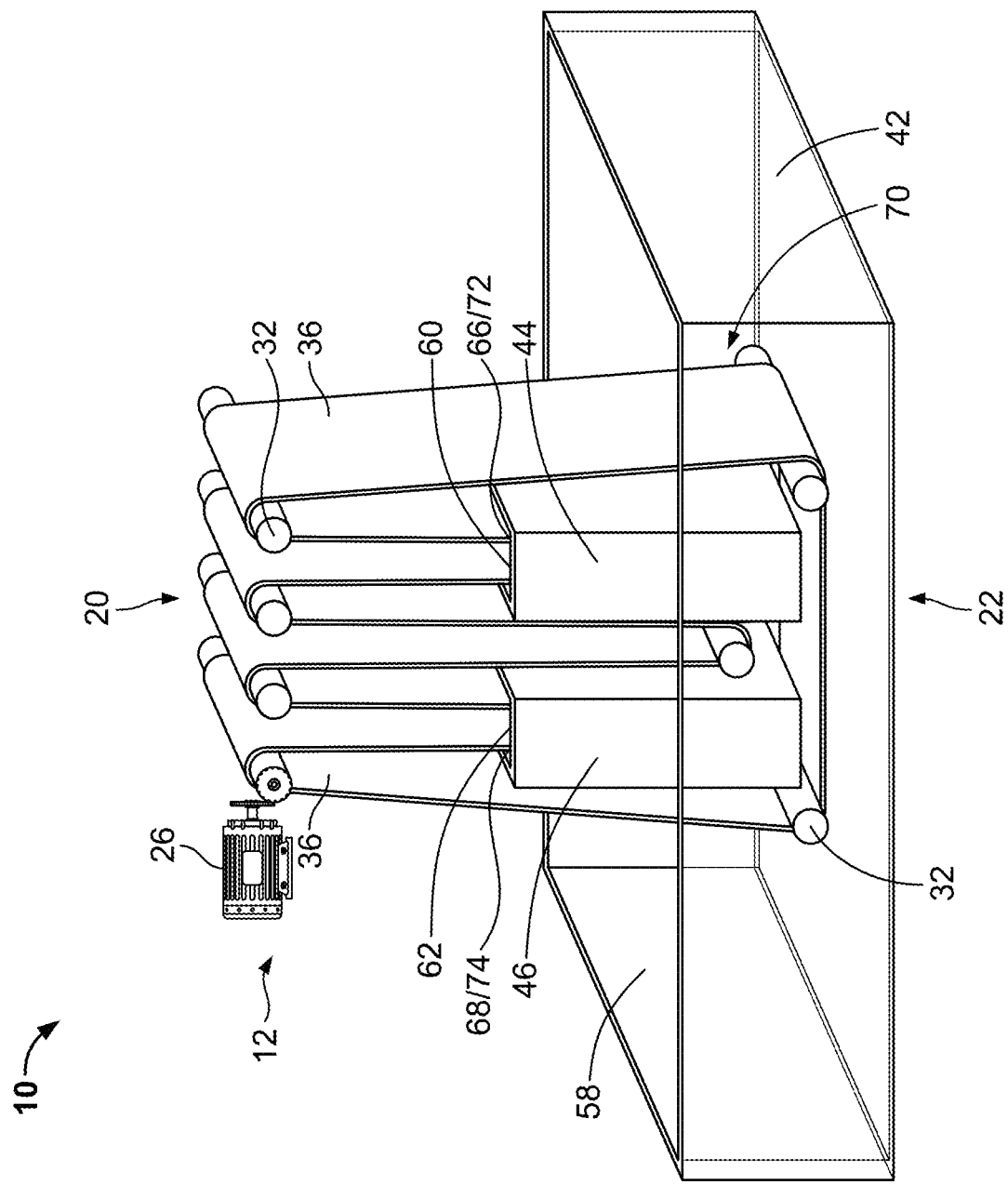
FIG. 2 depicts a perspective view of the system illustrated in FIG. 1 further comprising a motor.
Figure 3:
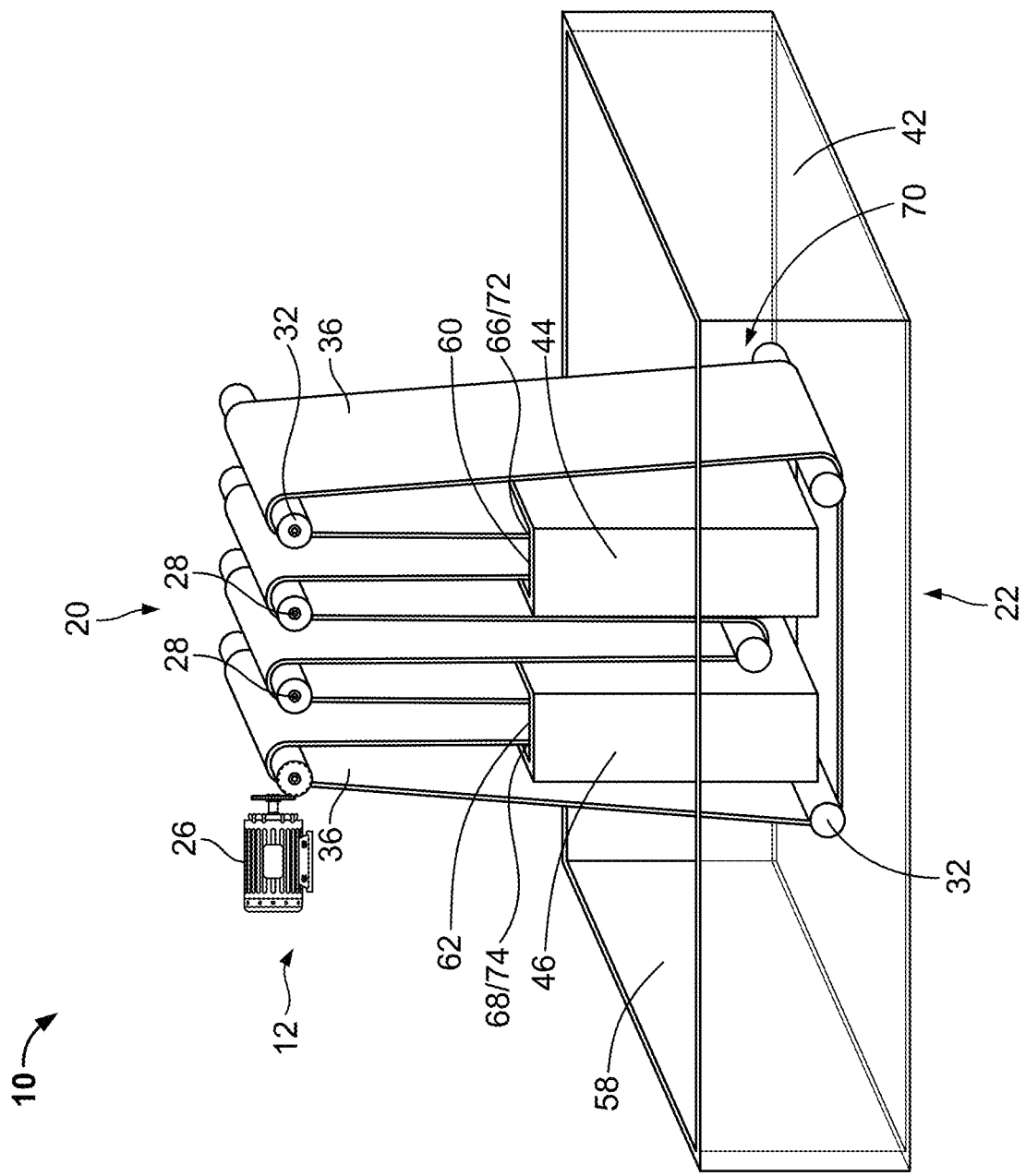
FIG. 3 depicts a perspective view of the system illustrated in FIG. 1 further comprising a motor and a plurality of drive shafts.
Figure 4:
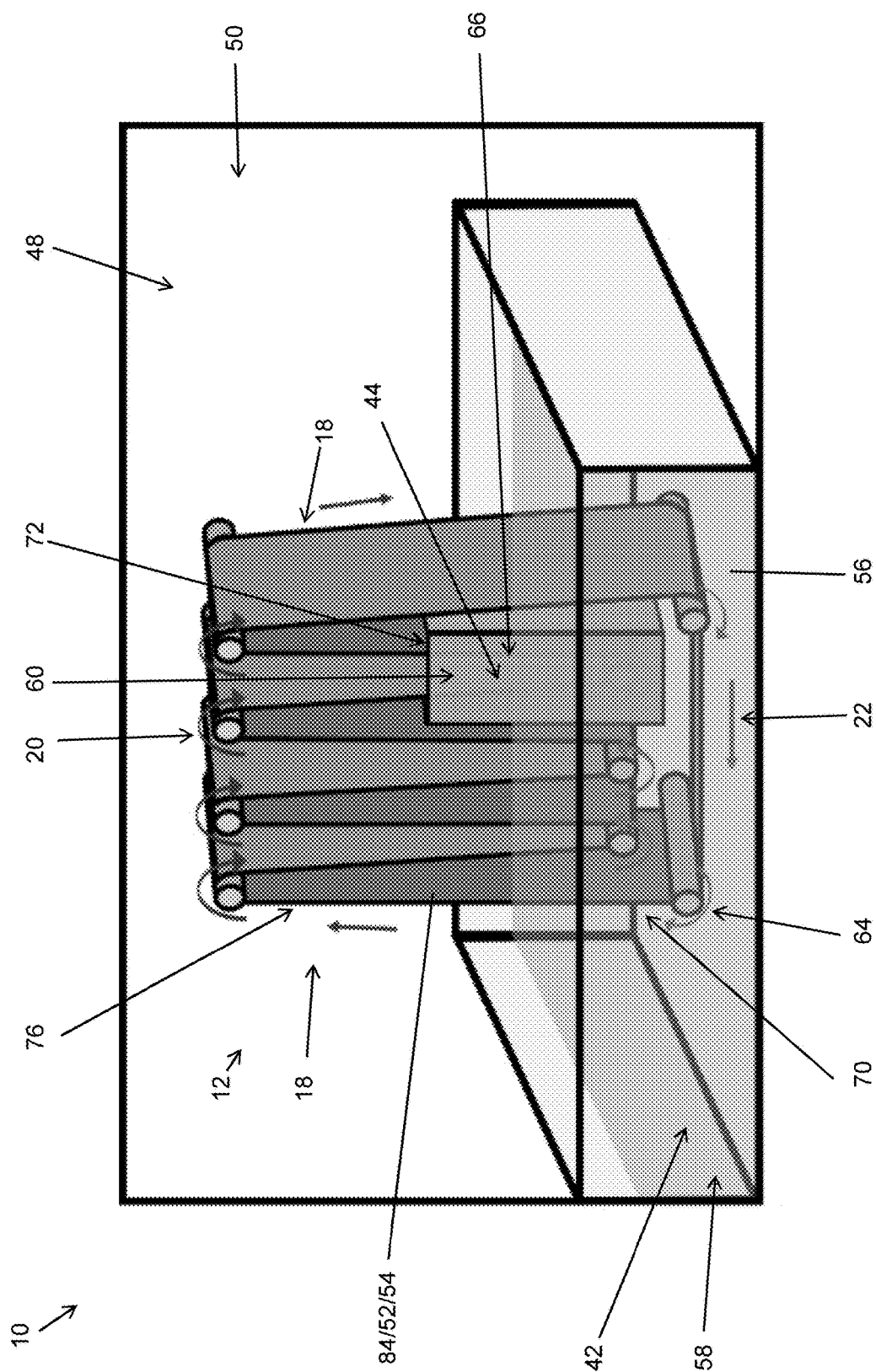
FIG. 4 depicts a perspective view of a system which utilizes microorganisms for removing a pollutant from a fluid wherein the system comprises two reservoirs.
Figure 5:
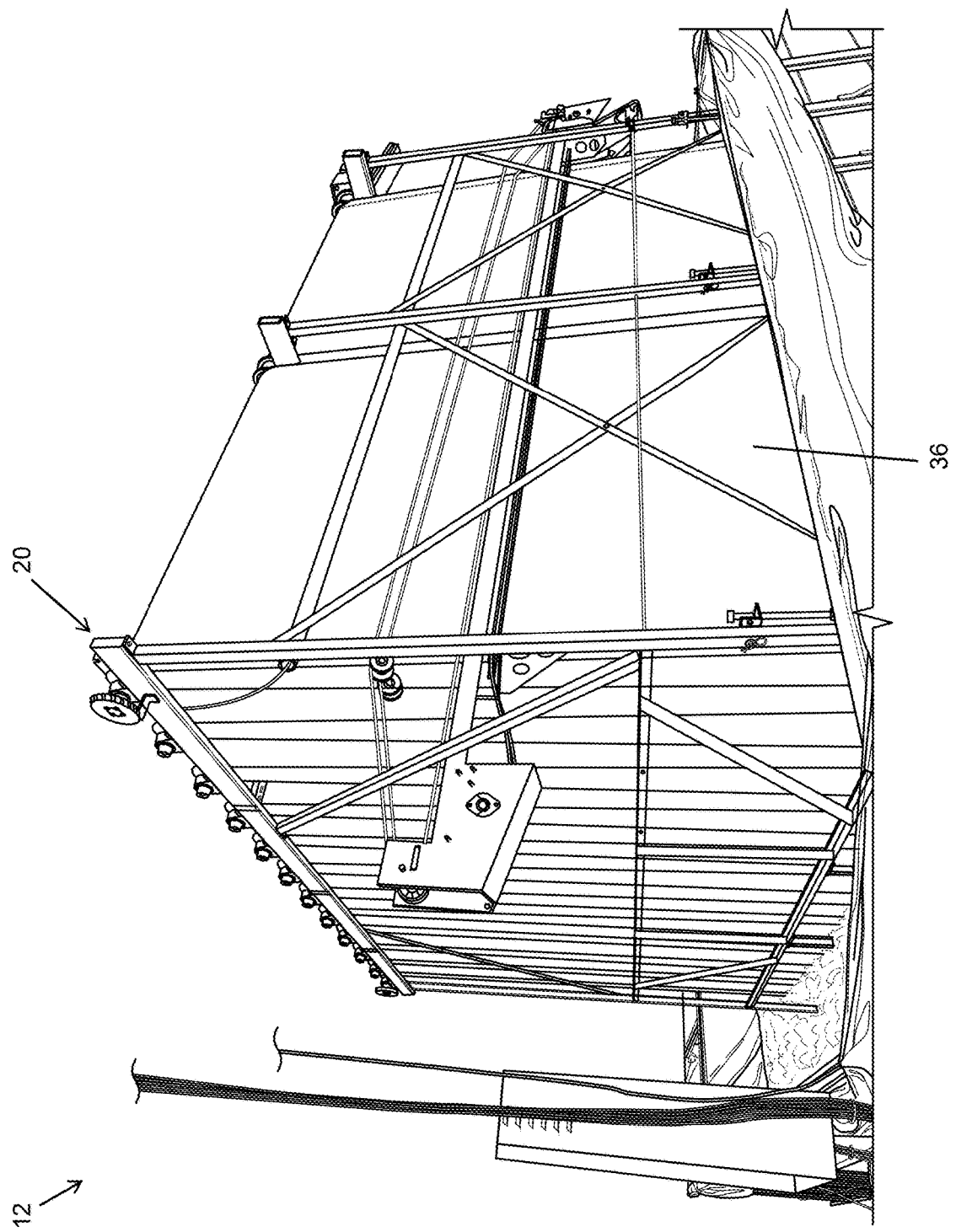
FIG. 5 depicts a perspective view of a microorganism growing apparatus according to one embodiment.
Figure 6:
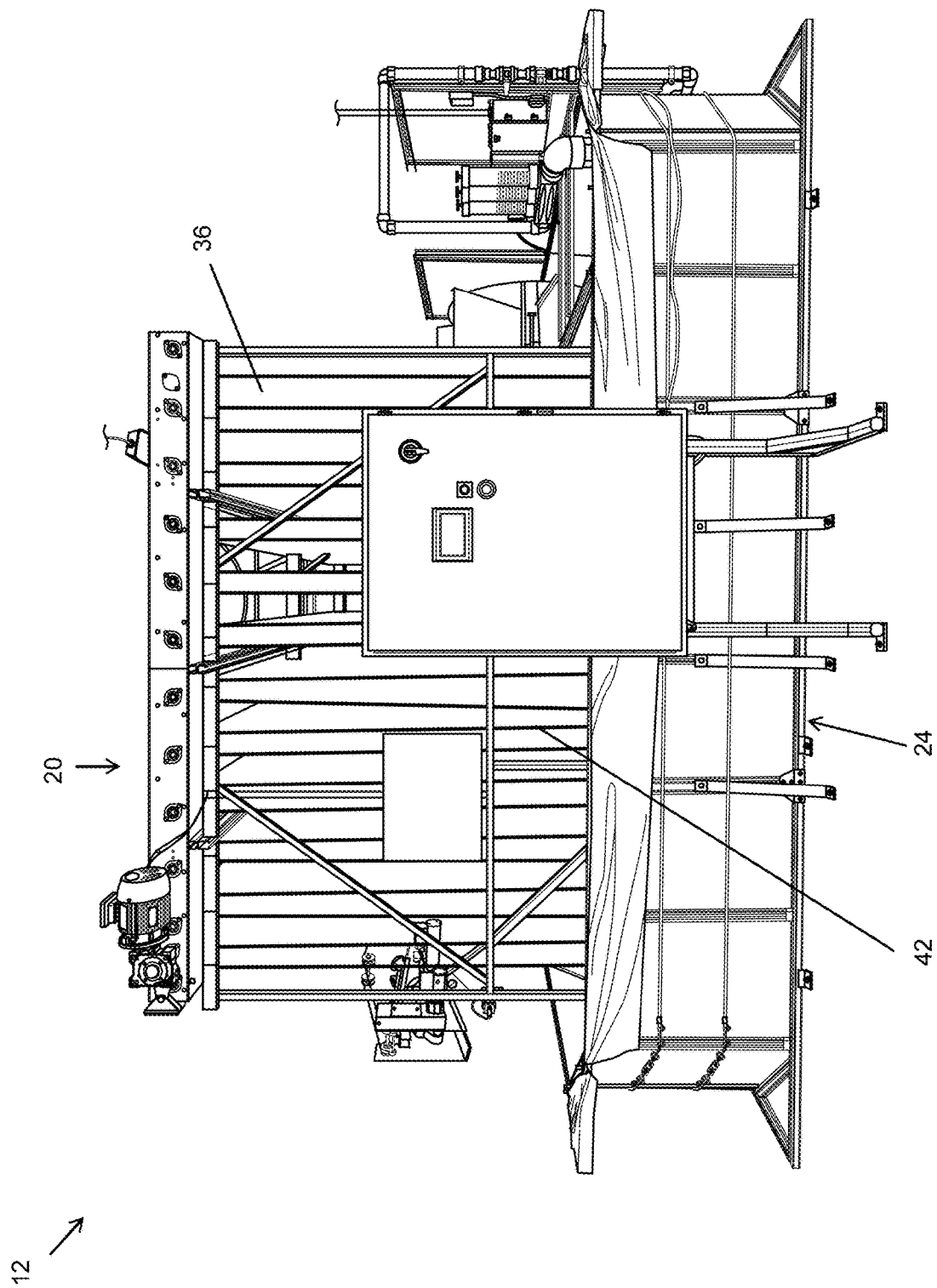
FIG. 6 depicts a perspective view of a microorganism growing apparatus according to one embodiment.
Figure 7:
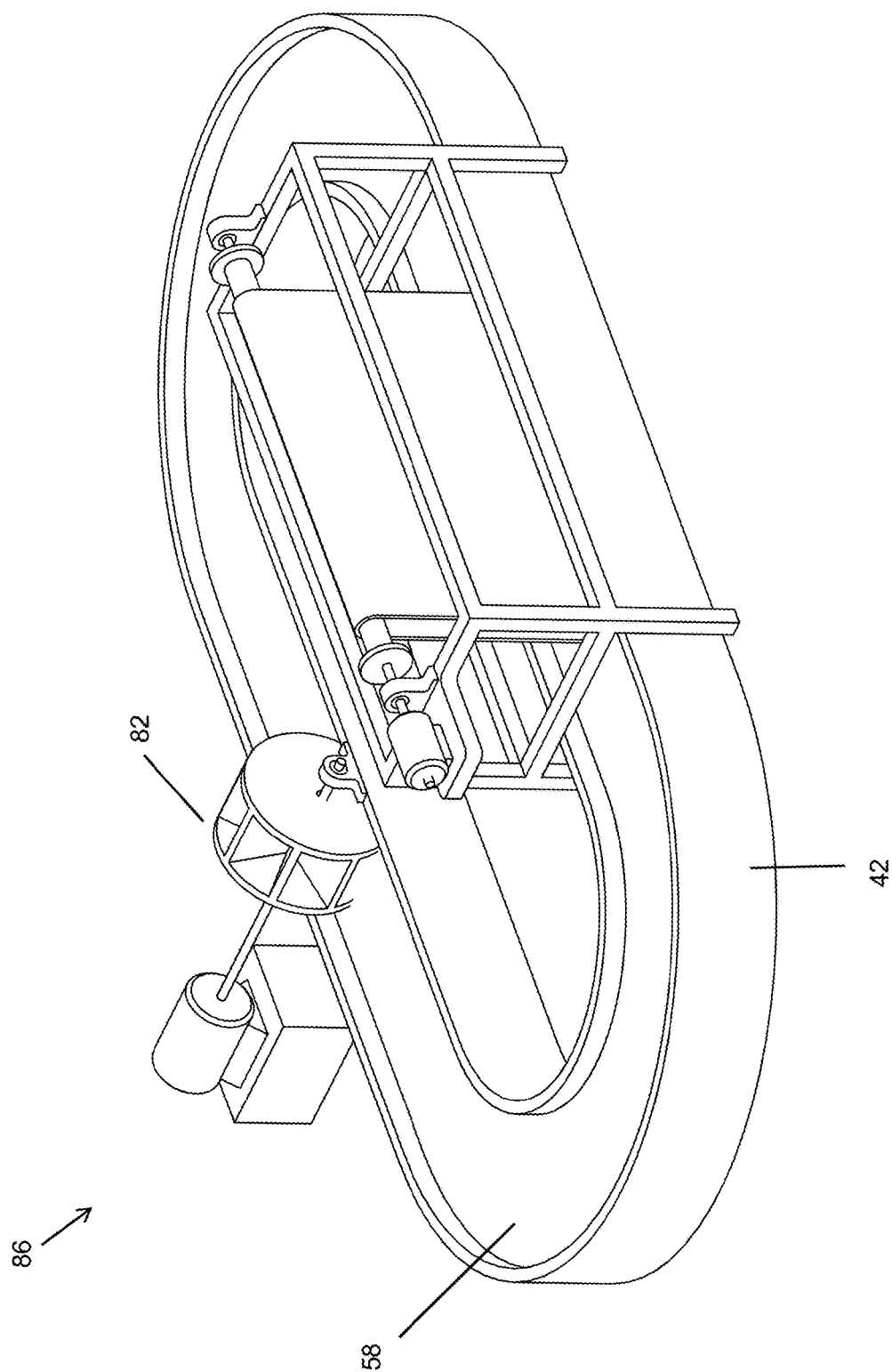
FIG. 7 depicts a perspective view of a trough system according to one embodiment.
Figure 8:
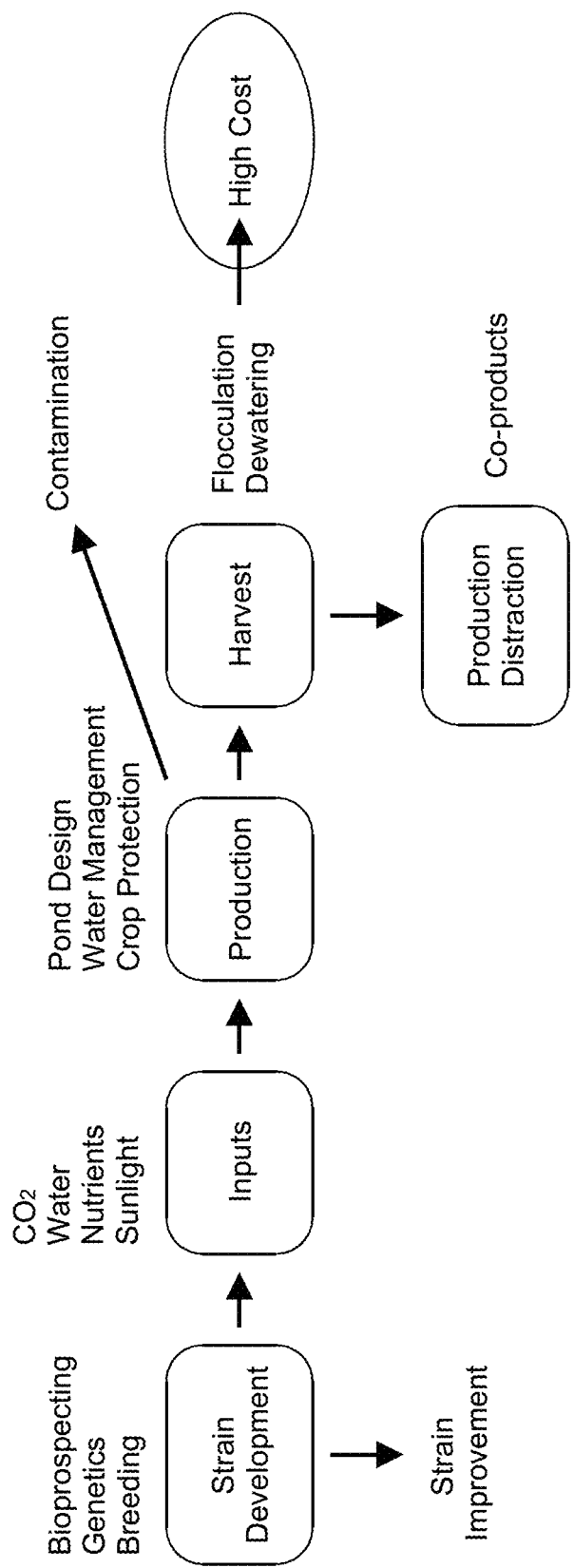
FIG. 8 depicts a flow chart illustrating the methodology generally associated with harvesting of microorganisms such as algae.
Figure 9:
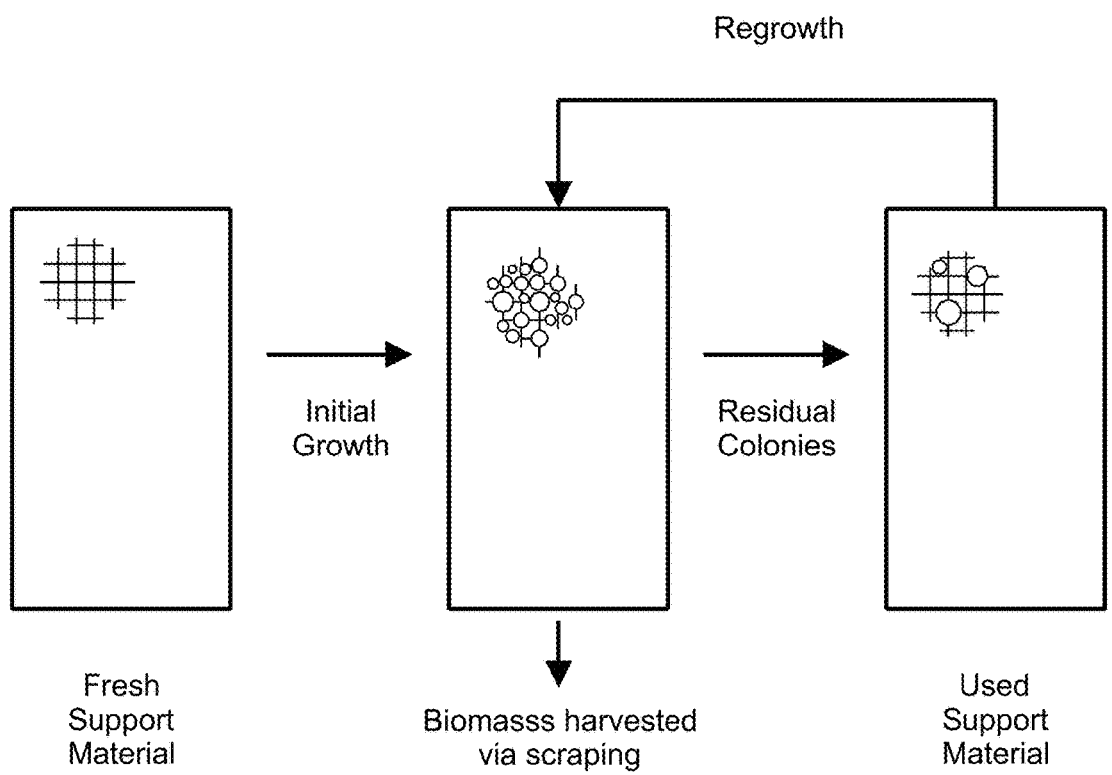
FIG. 9 depicts a top view of a microorganism, such as algae, being grown on a moving belt.
Figure 10:
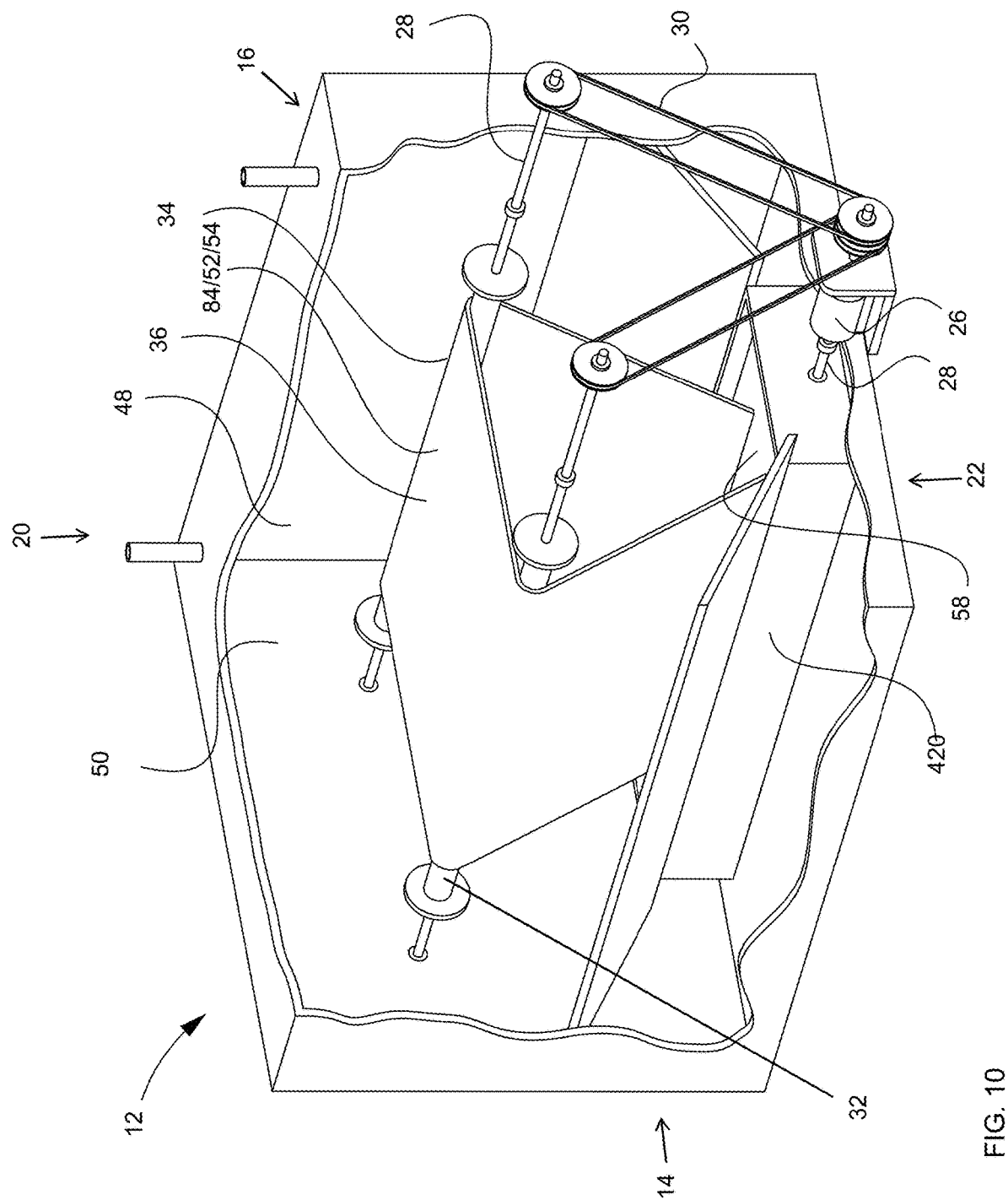
FIG. 10 depicts a partial cutaway perspective view of a microorganism growing apparatus according to one embodiment.
Figure 11:
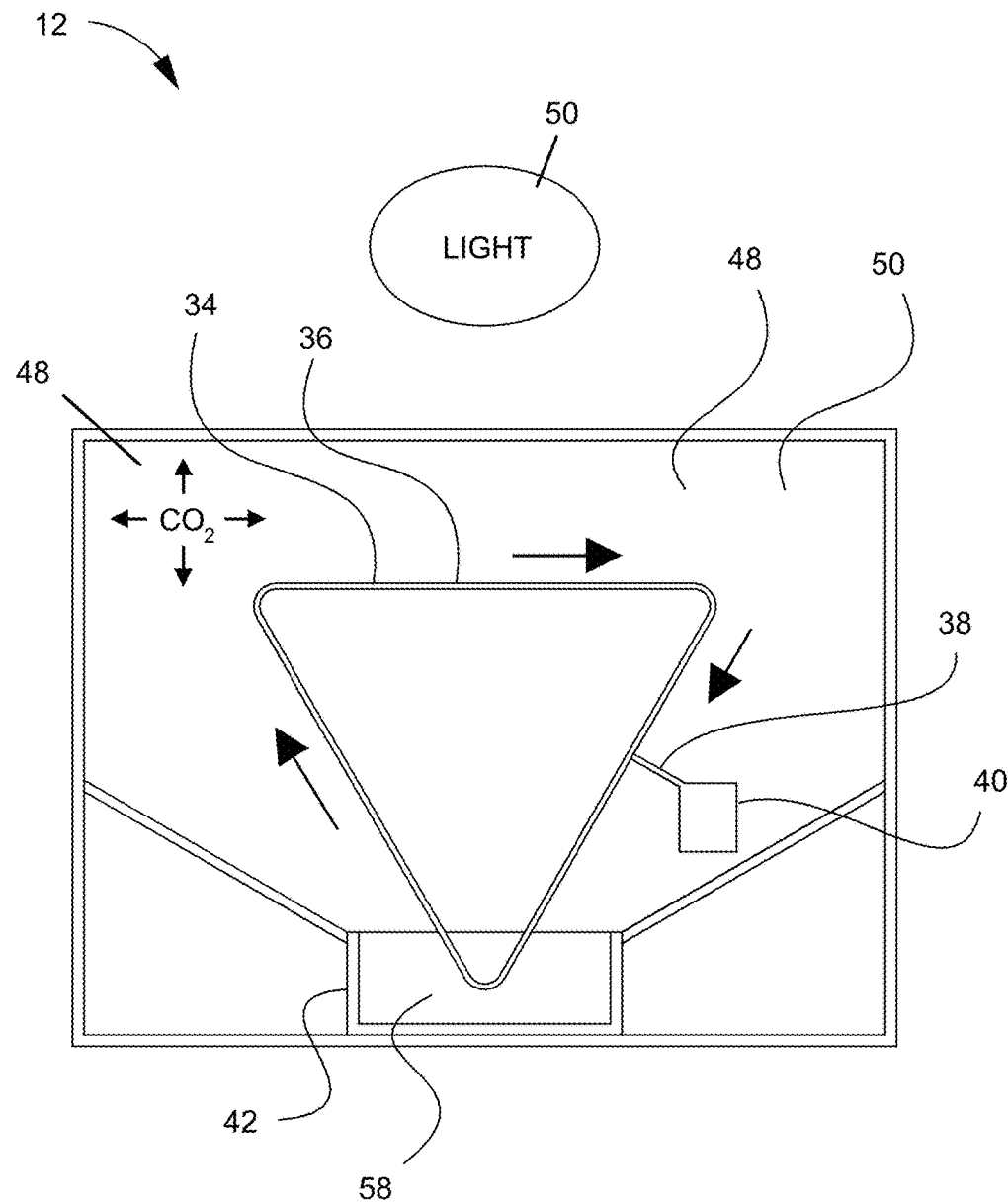
FIG. 11 depicts a schematic front view of the microorganism growing apparatus illustrated in FIG. 10.
Figure 12:
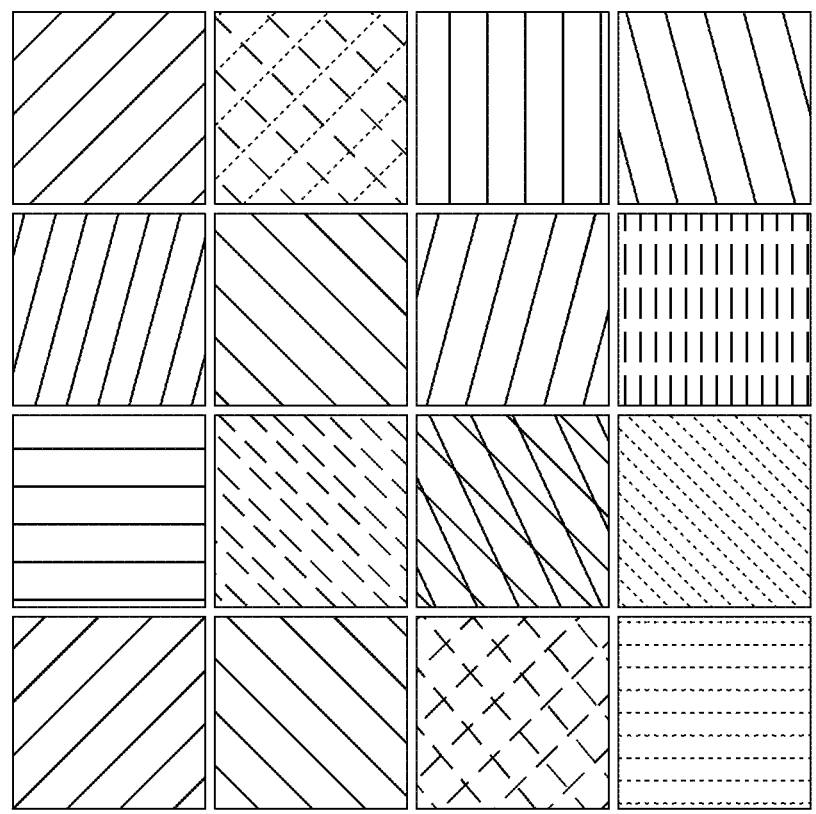
FIG. 12 depicts a top view of a microorganism being grown on a variety of materials which may be used to form the at least one moving belt.
Figure 13:
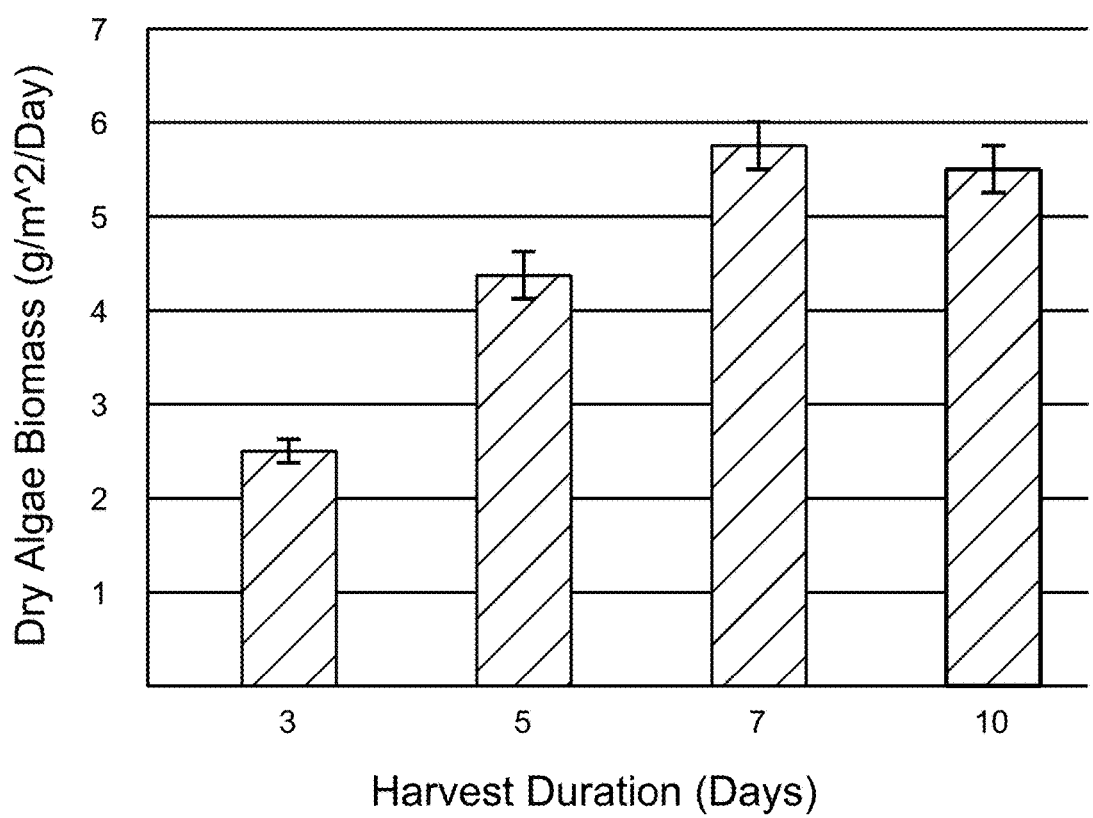
FIG. 13 depicts a bar chart of harvesting frequencies for an algal strain according to one embodiment.
Figure 14:
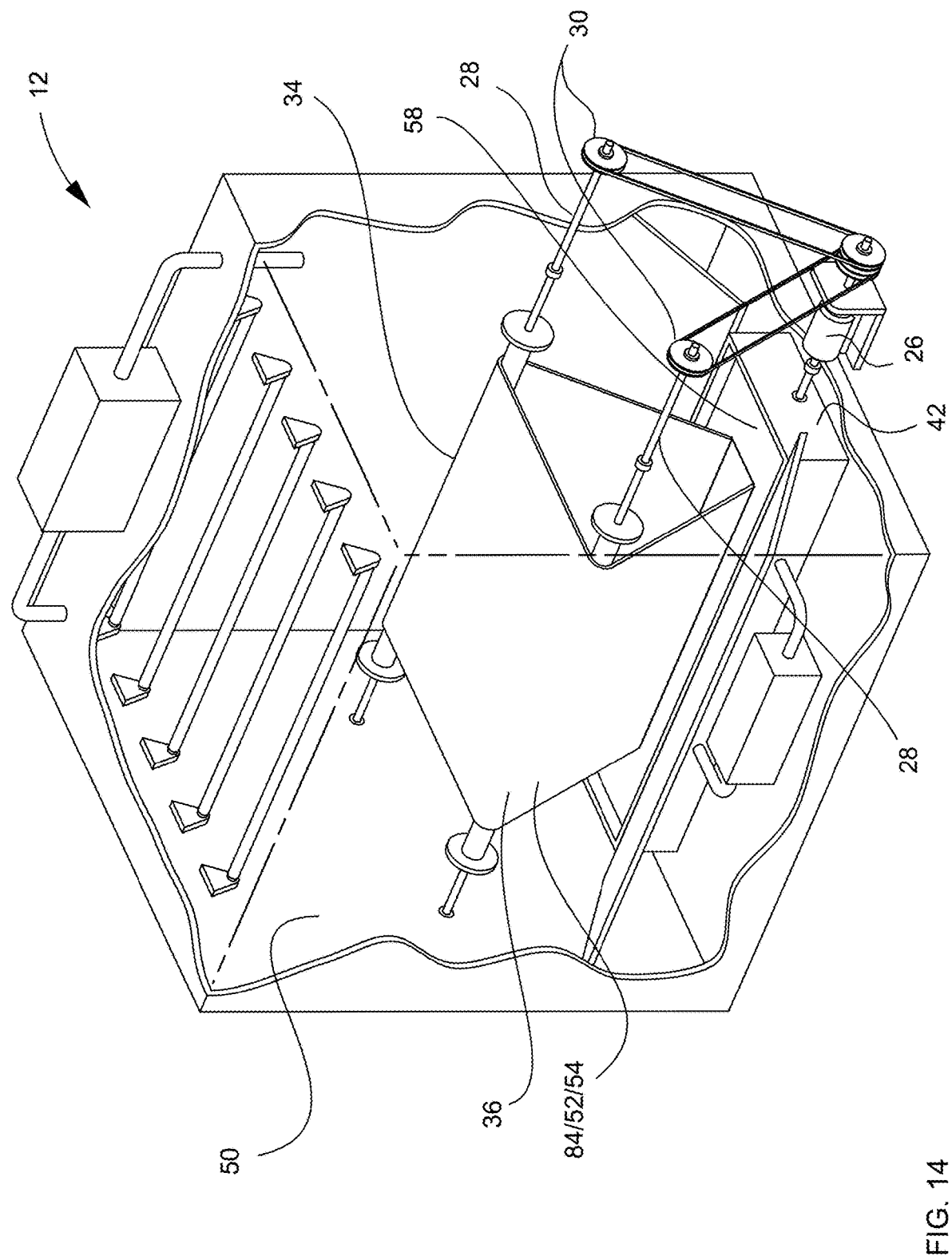
FIG. 14 depicts a partial cutaway perspective view of the microorganism growing apparatus illustrated in FIG. 10, shown with grow lights and gas input.
Figure 15:
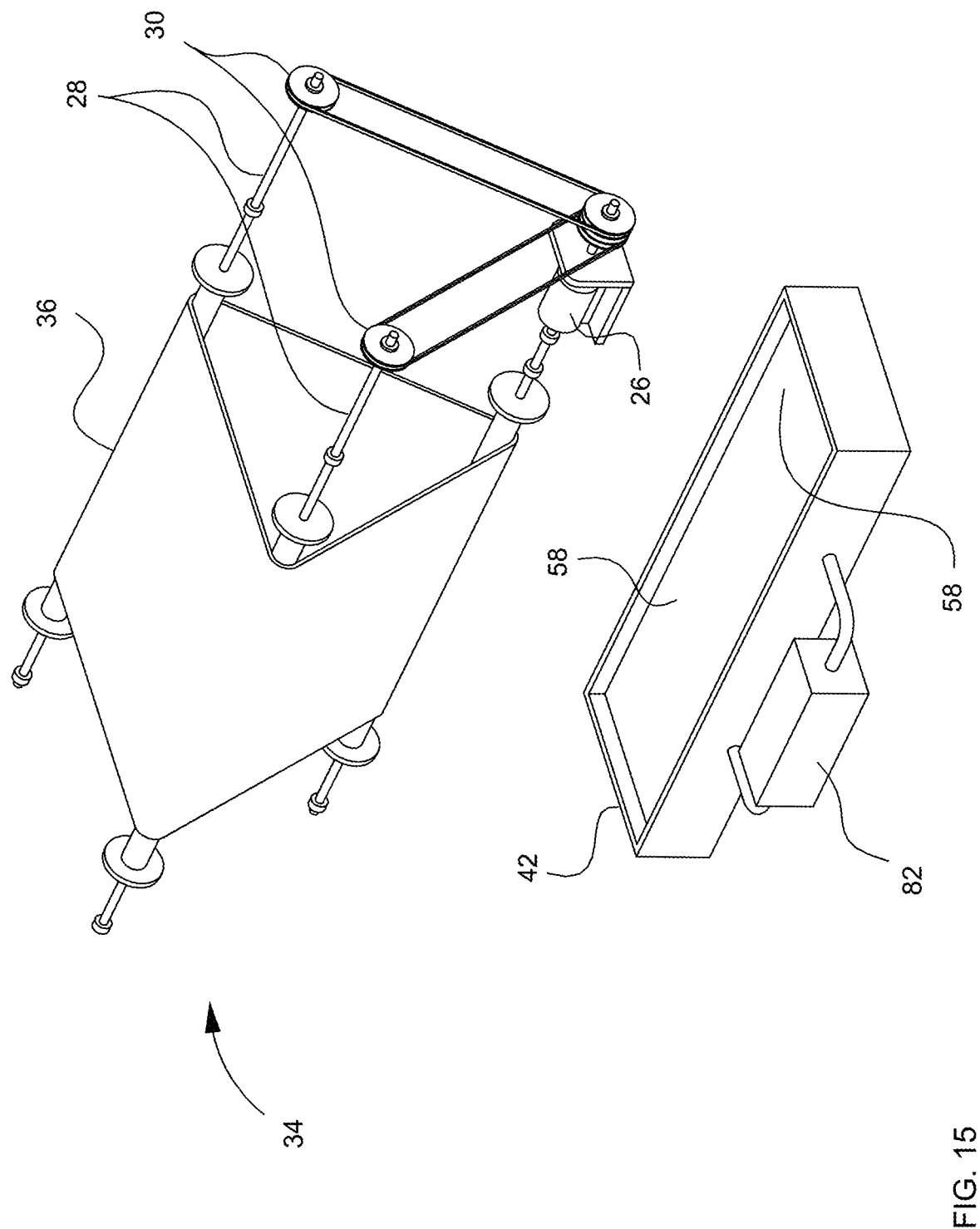
FIG. 15 depicts a partial exploded view of the microorganism growing apparatus shown in FIG. 10.
Figure 16:
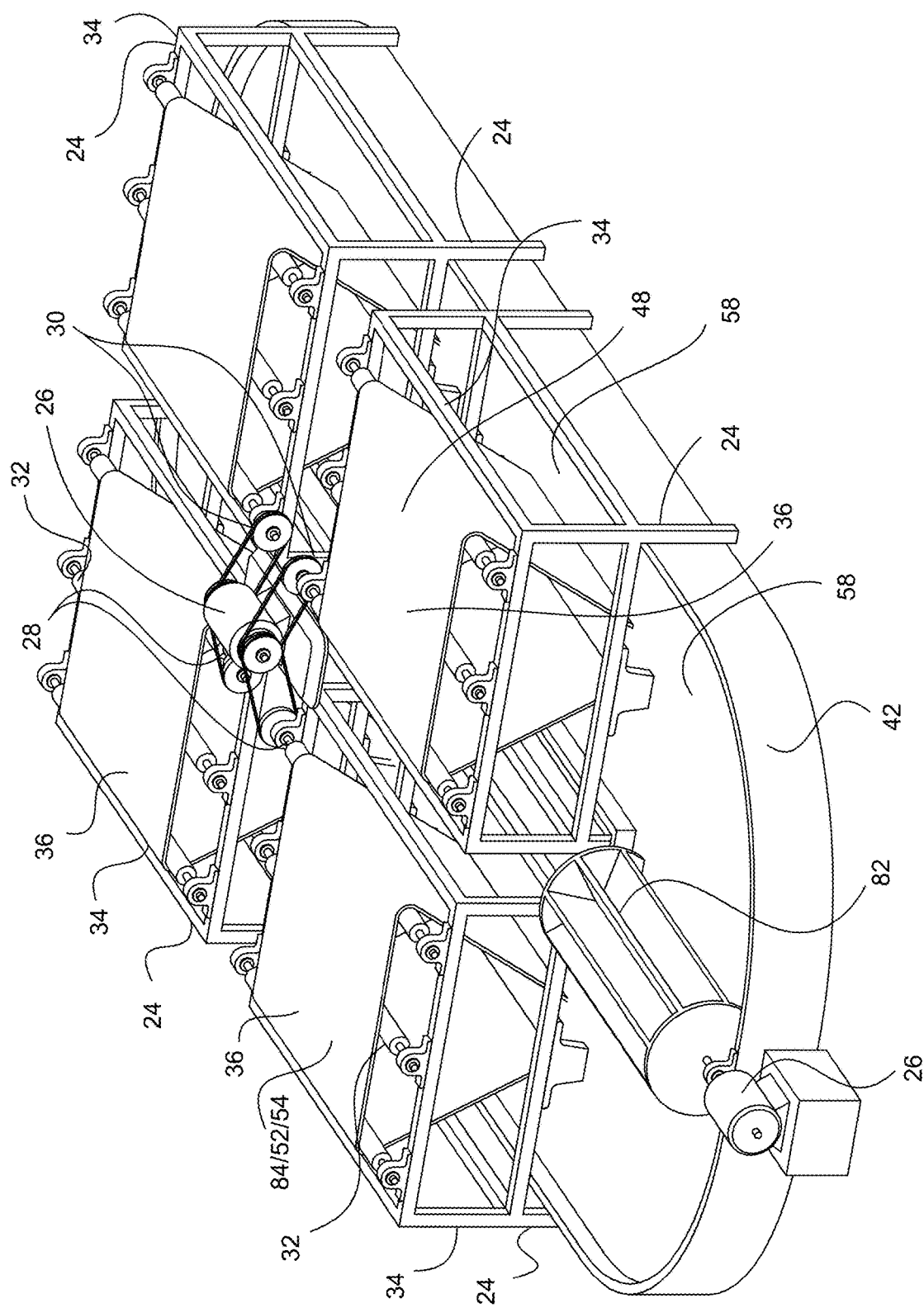
FIG. 16 depicts a perspective view of a system having a plurality of associated microorganism growing apparatuses and a trough system according to one embodiment.
Figure 17:
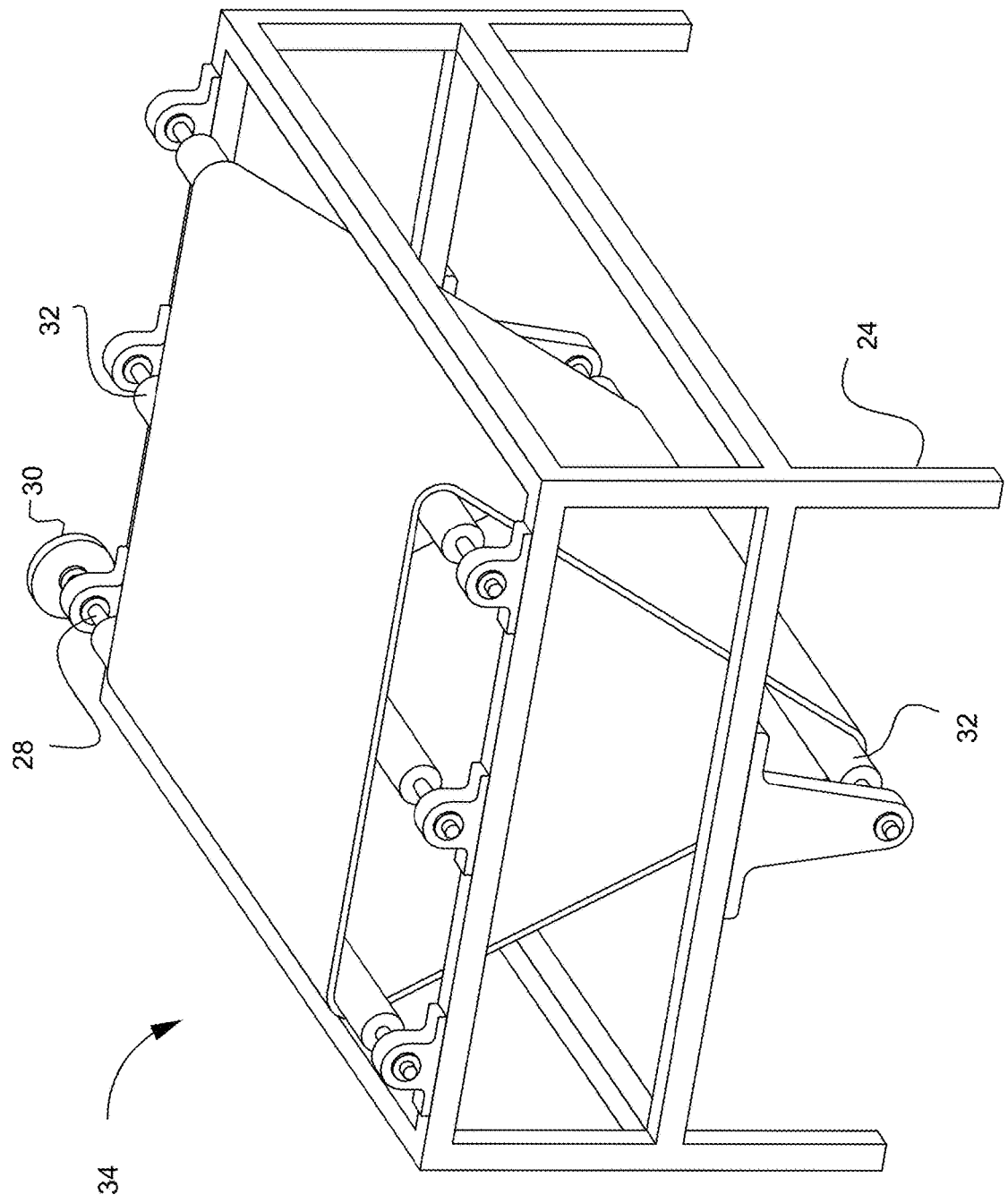
FIG. 17 depicts a perspective view of a microorganism growing apparatus as illustrated in FIG. 19.
Figure 18:
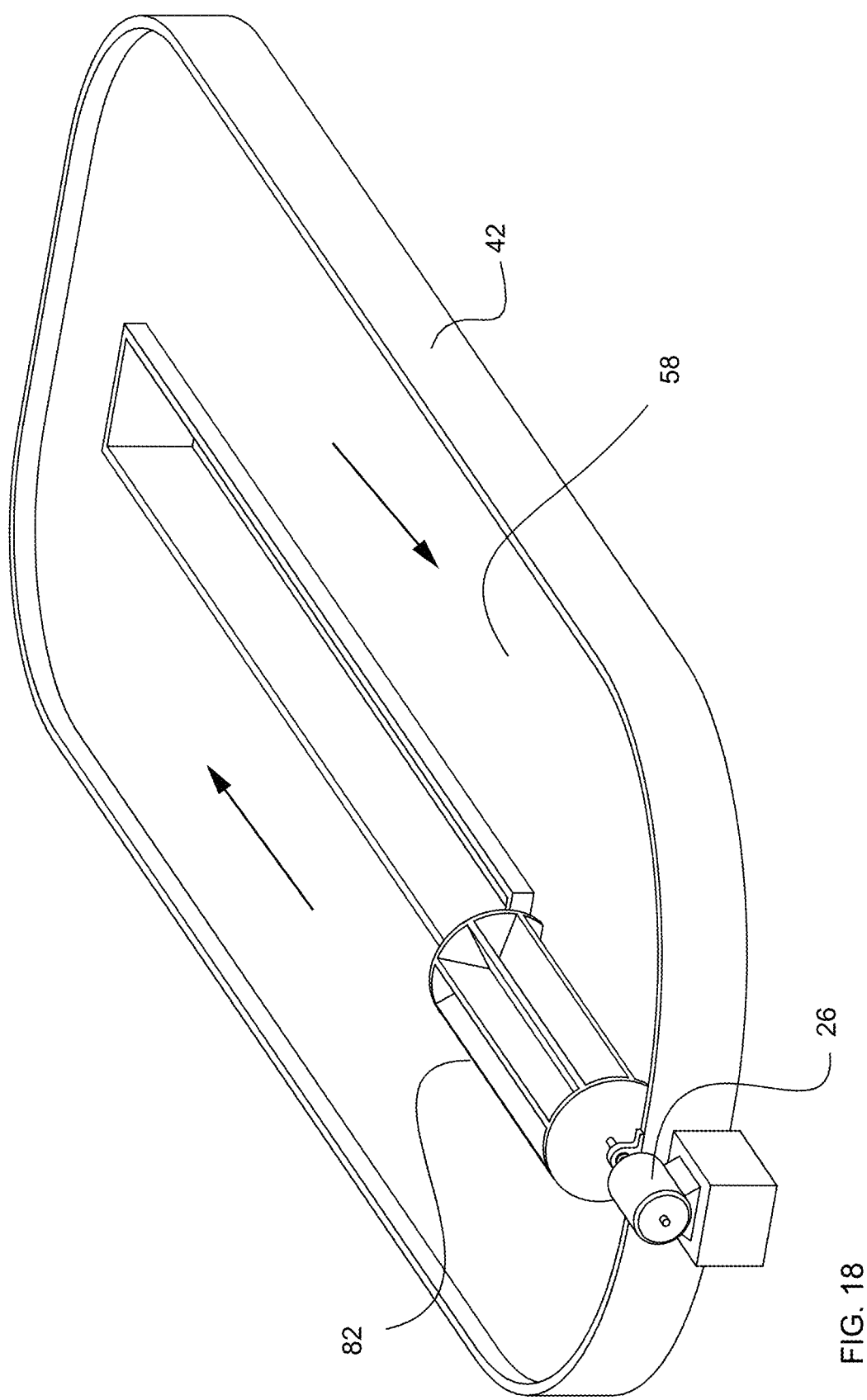
FIG. 18 depicts a perspective view of a trough system as illustrated in FIG. 19.
Figure 19:
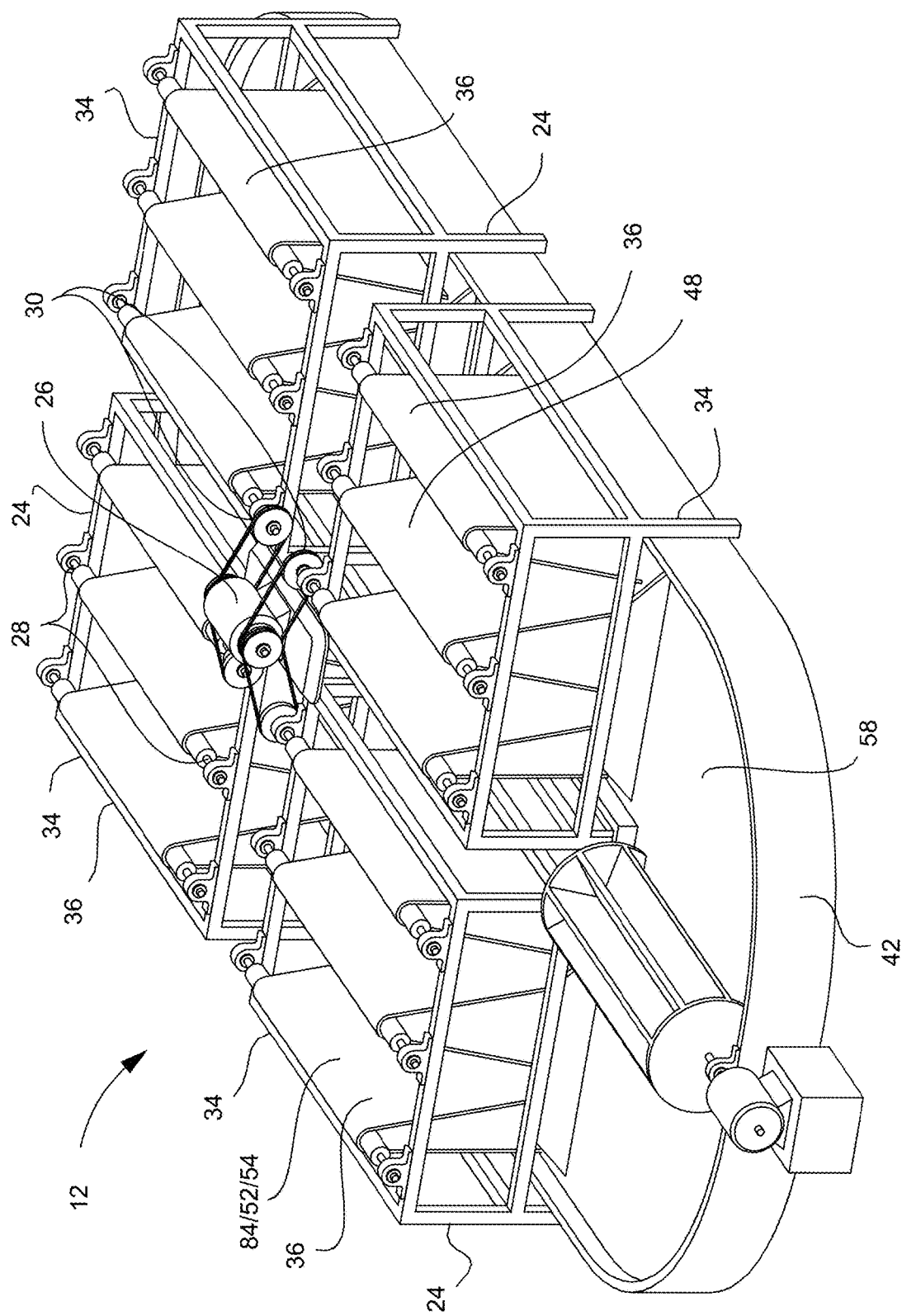
FIG. 19 depicts a perspective view of a system having a plurality of associated microorganism growing apparatuses and a trough system according to an alternate embodiment.
Figure 20:
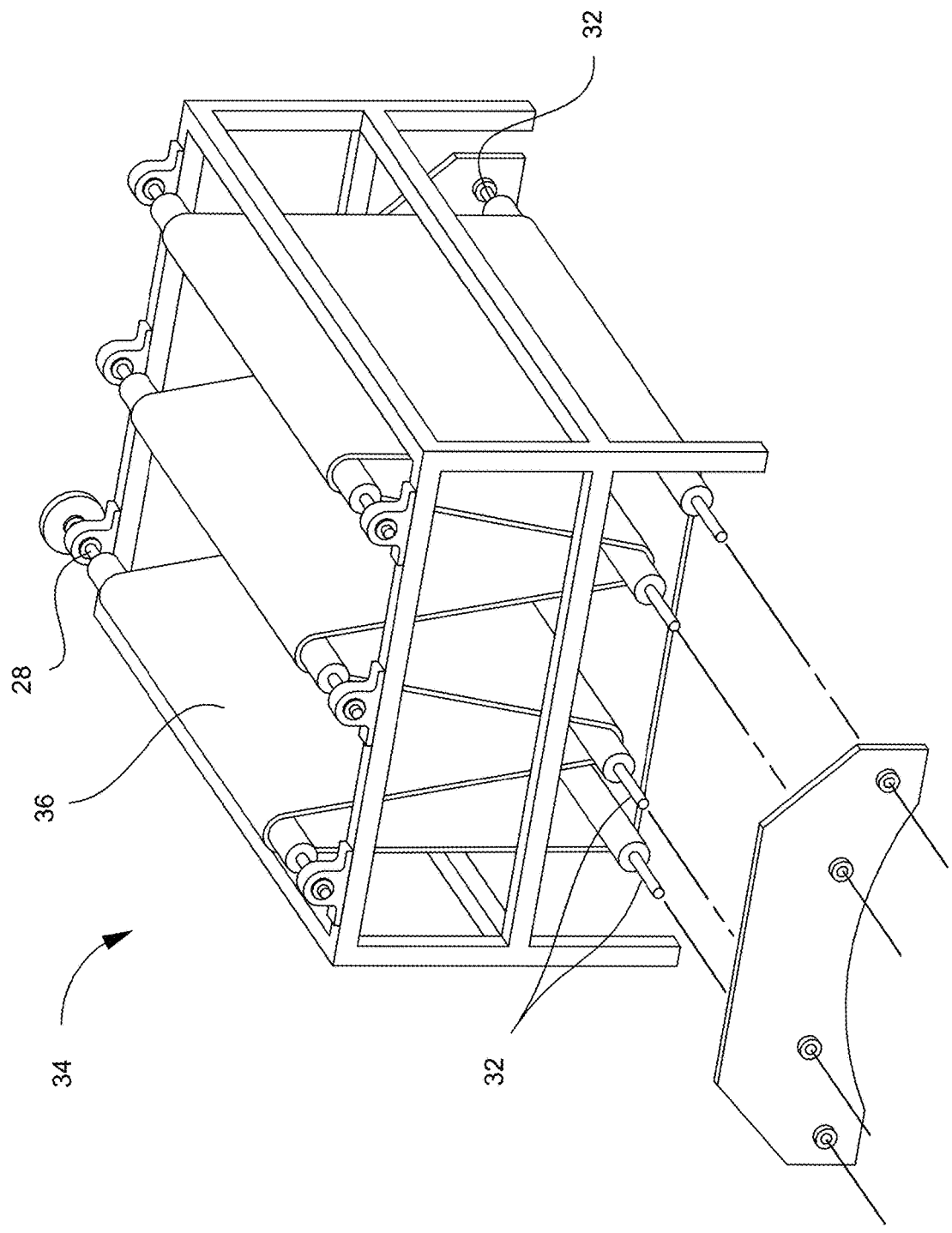
FIG. 20 depicts a perspective view of a microorganism growing apparatus as illustrated in FIG. 19.
Figure 21:
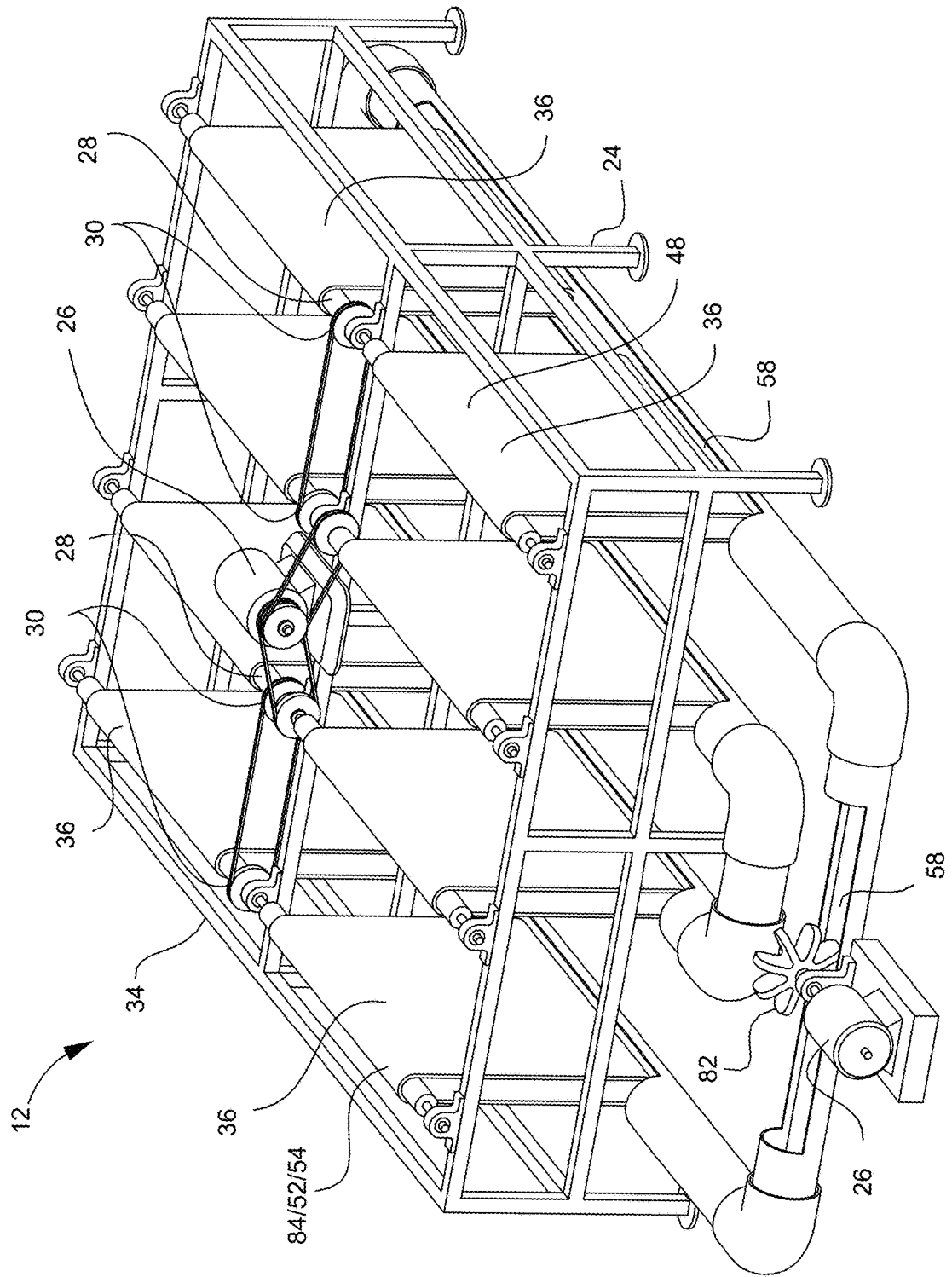
FIG. 21 depicts a perspective view of a system having associated microorganism growing apparatuses and a trough system according to one embodiment.
Figure 22:
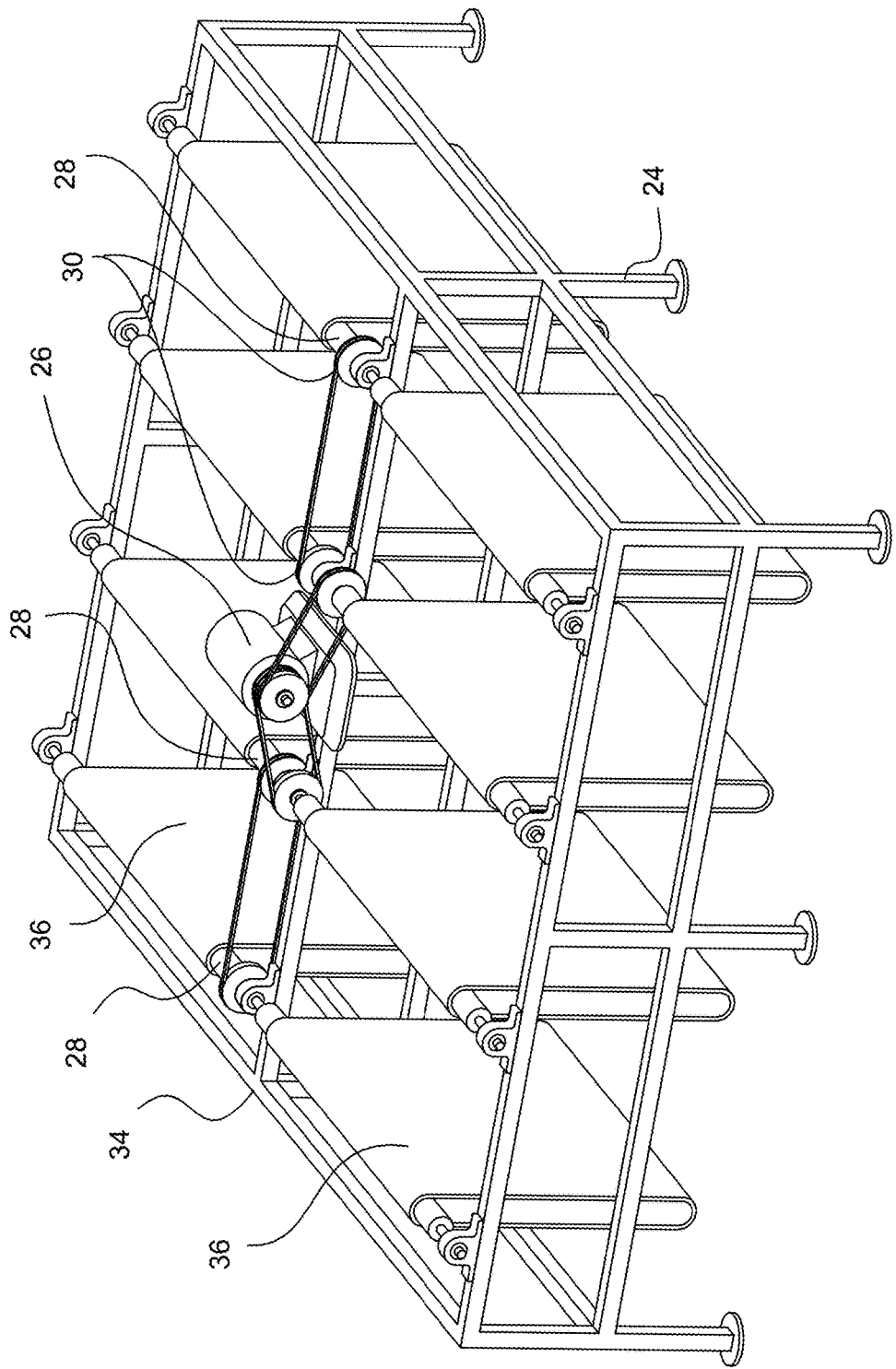
FIG. 22 depicts a perspective view of the system having associated microorganism growing apparatuses as illustrated in FIG. 21.
Figure 23:
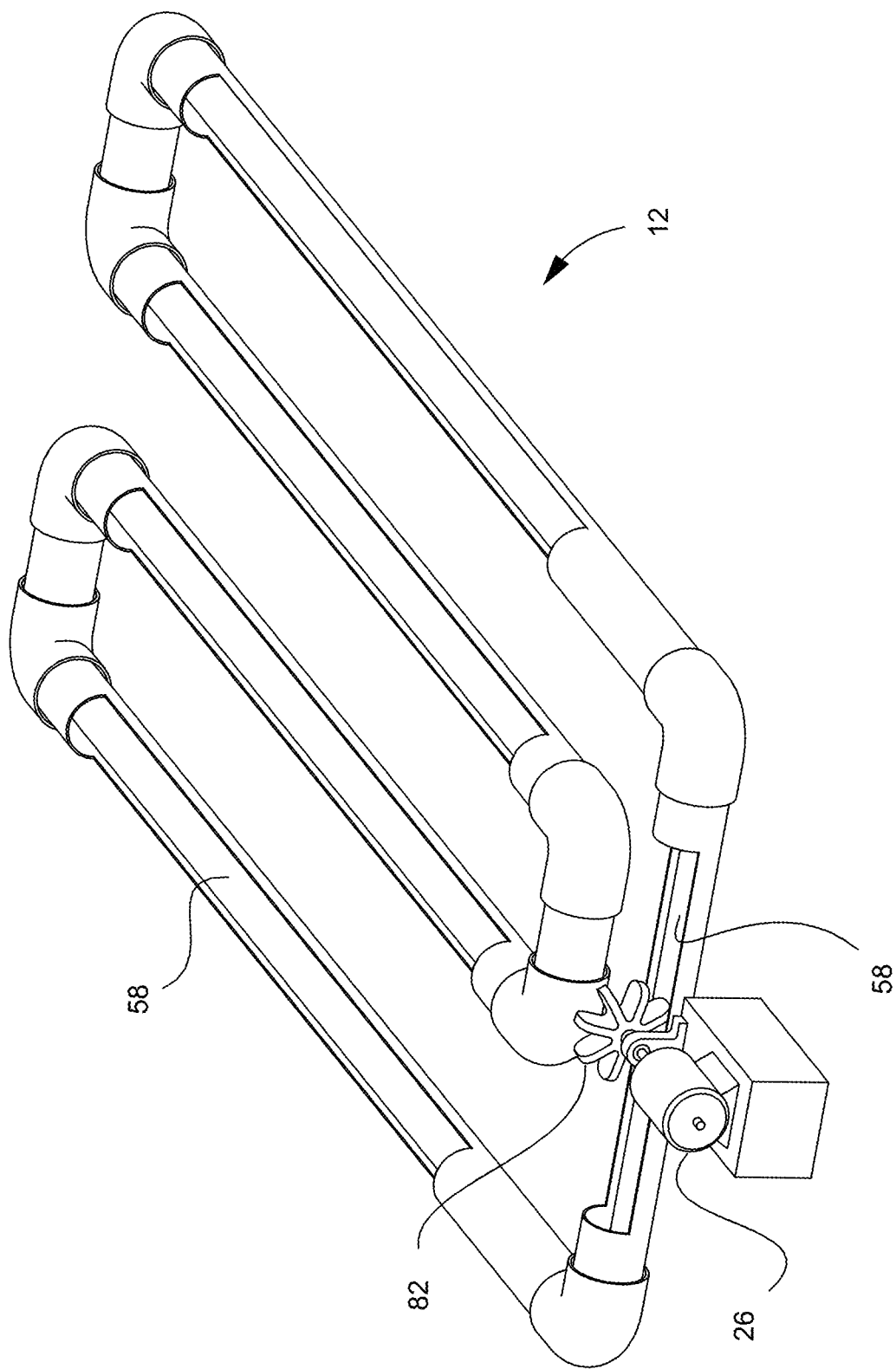
FIG. 23 depicts a perspective view of the trough system illustrated in FIG. 21.
Figure 24:
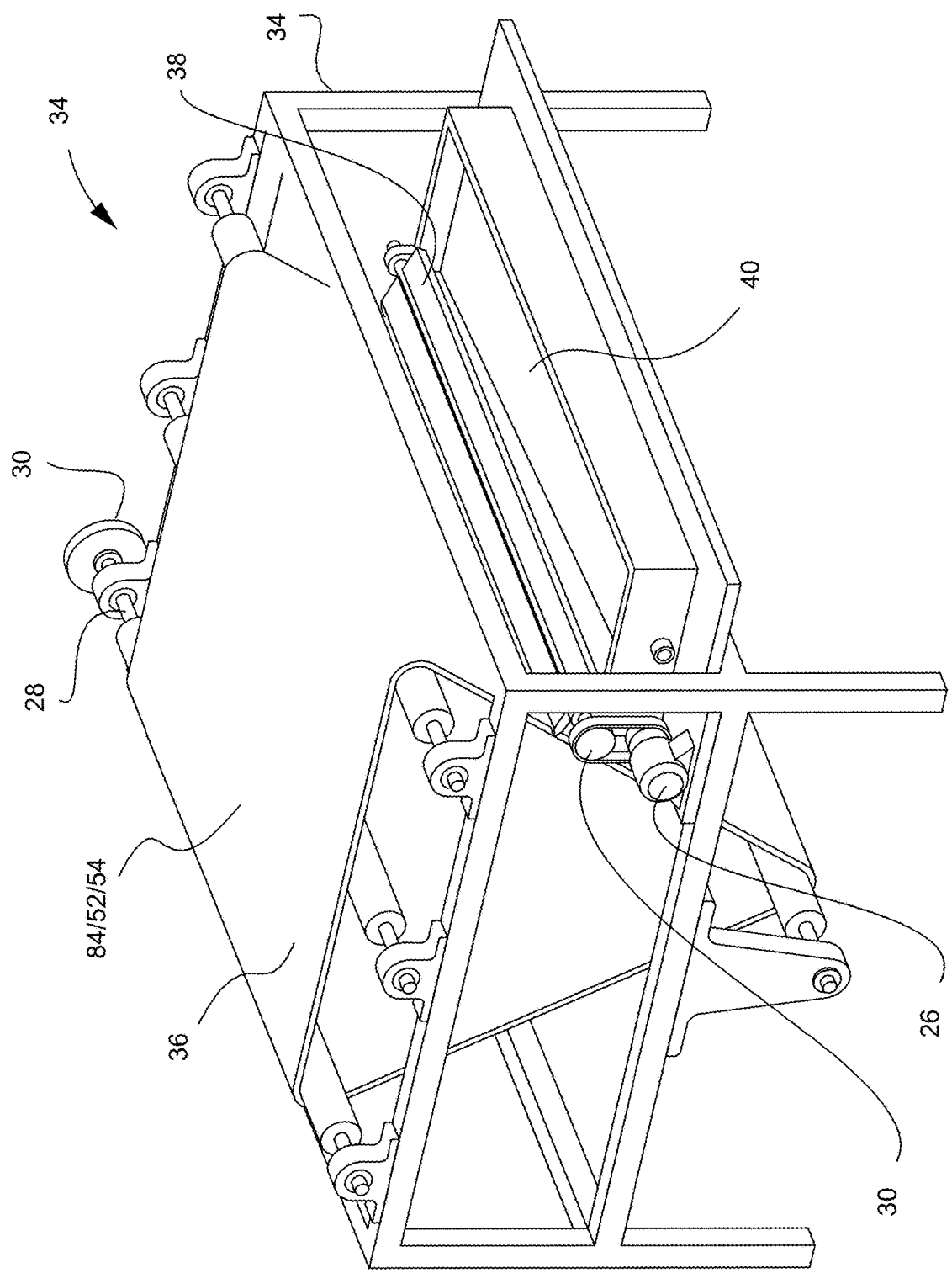
FIG. 24 depicts a perspective view of a microorganism growing apparatus shown with a mechanized harvesting system according to one embodiment.
Figure 25:
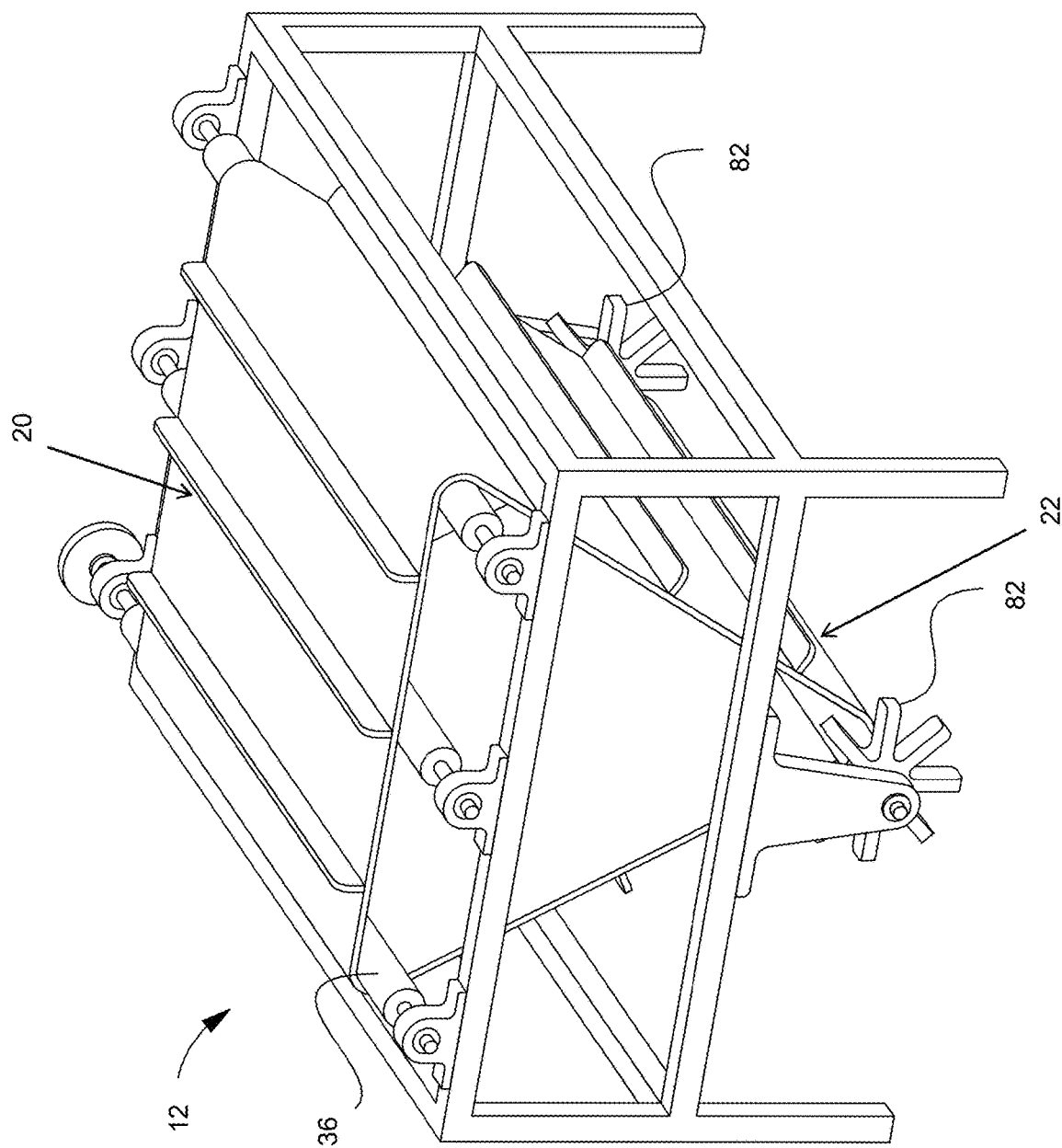
FIG. 25 depicts a perspective view of a microorganism growing apparatus according to one embodiment.
Figure 26:
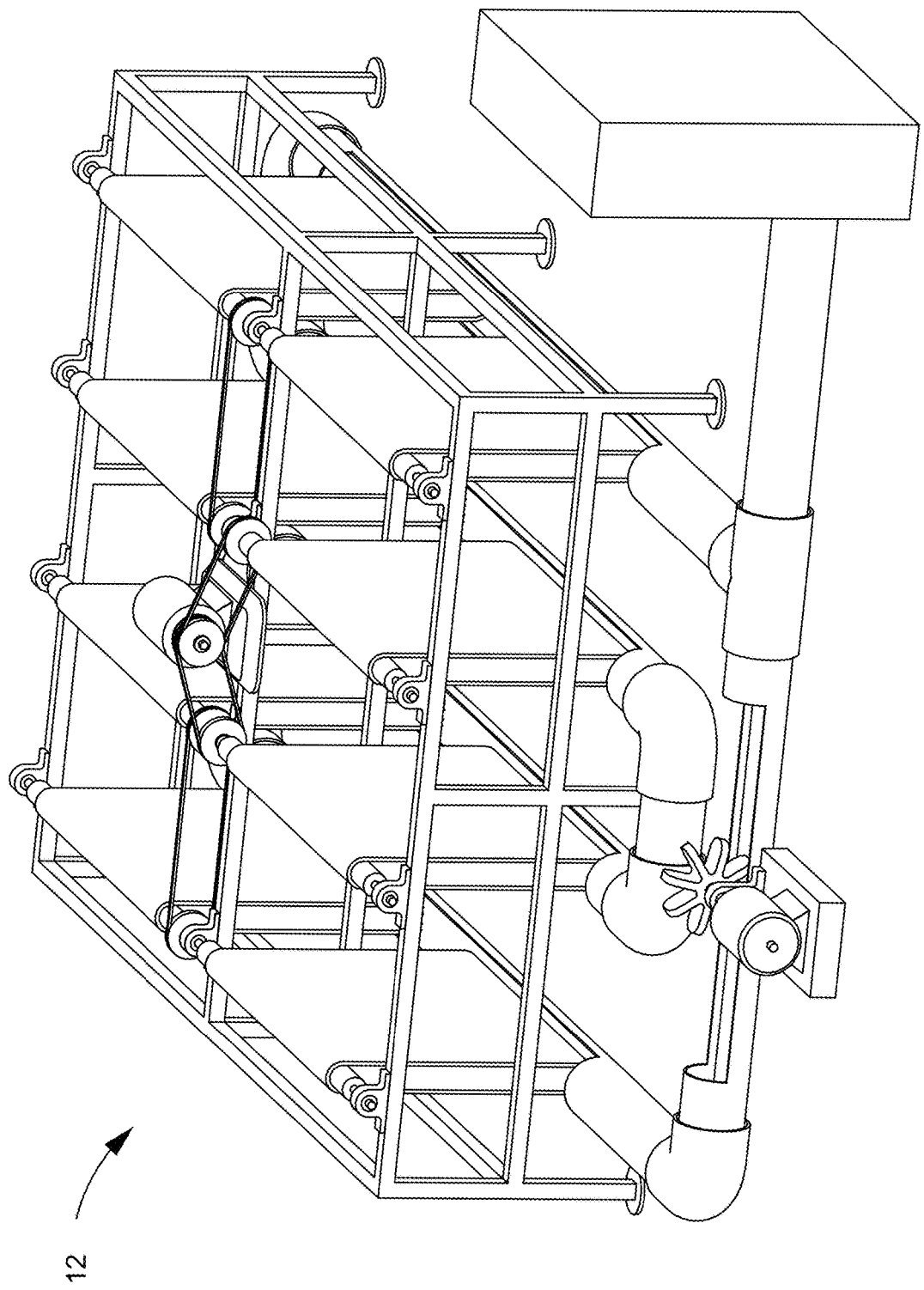
FIG. 26 depicts a perspective view of a system according to one embodiment.
Figure 36:
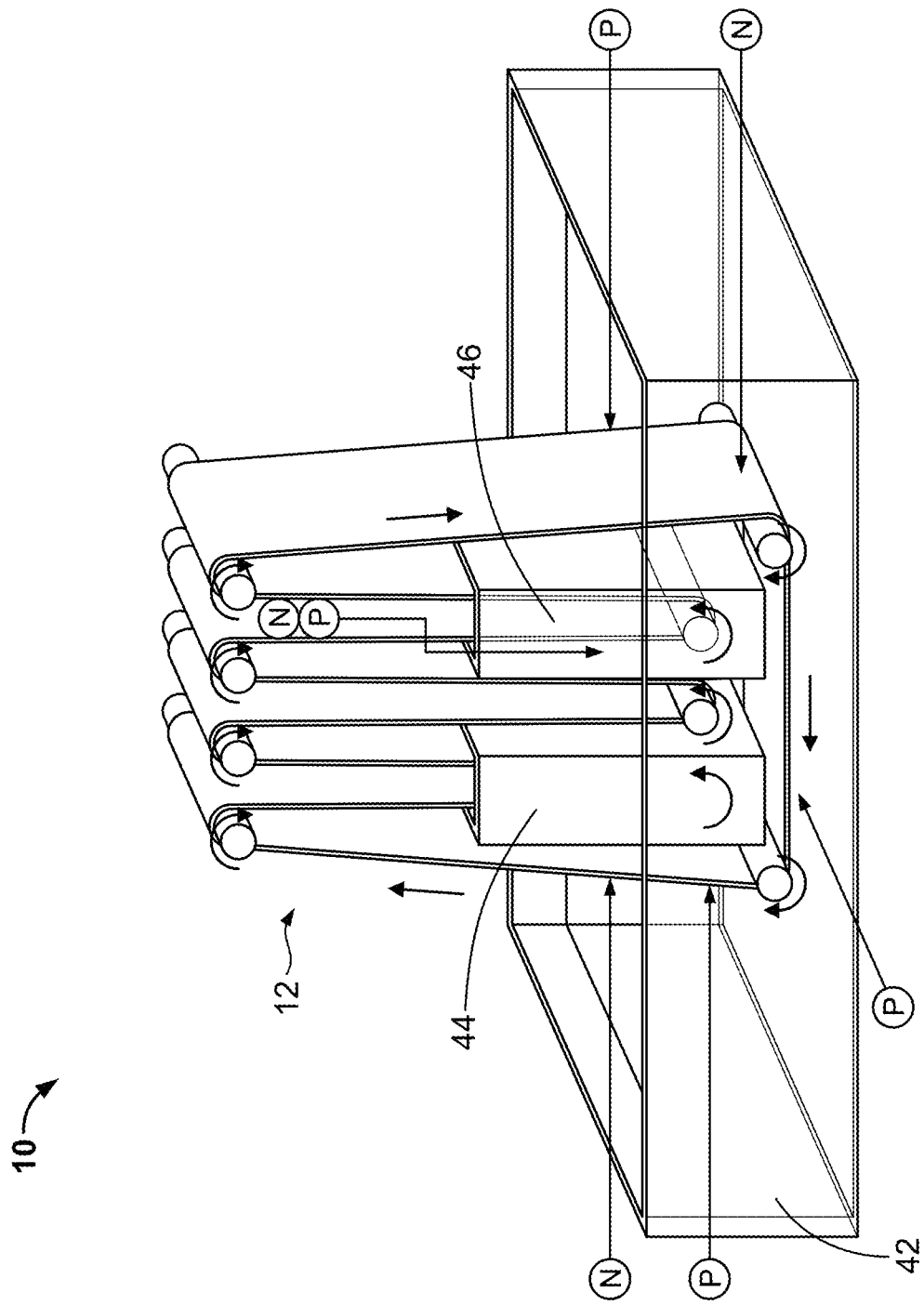
FIG. 36 depicts a perspective view of a system which utilizes microorganisms for removing a pollutant from a fluid according to one embodiment; wherein the system comprises a first reservoir for pollutant uptake and a second reservoir for release of the pollutant.
Figure 37:
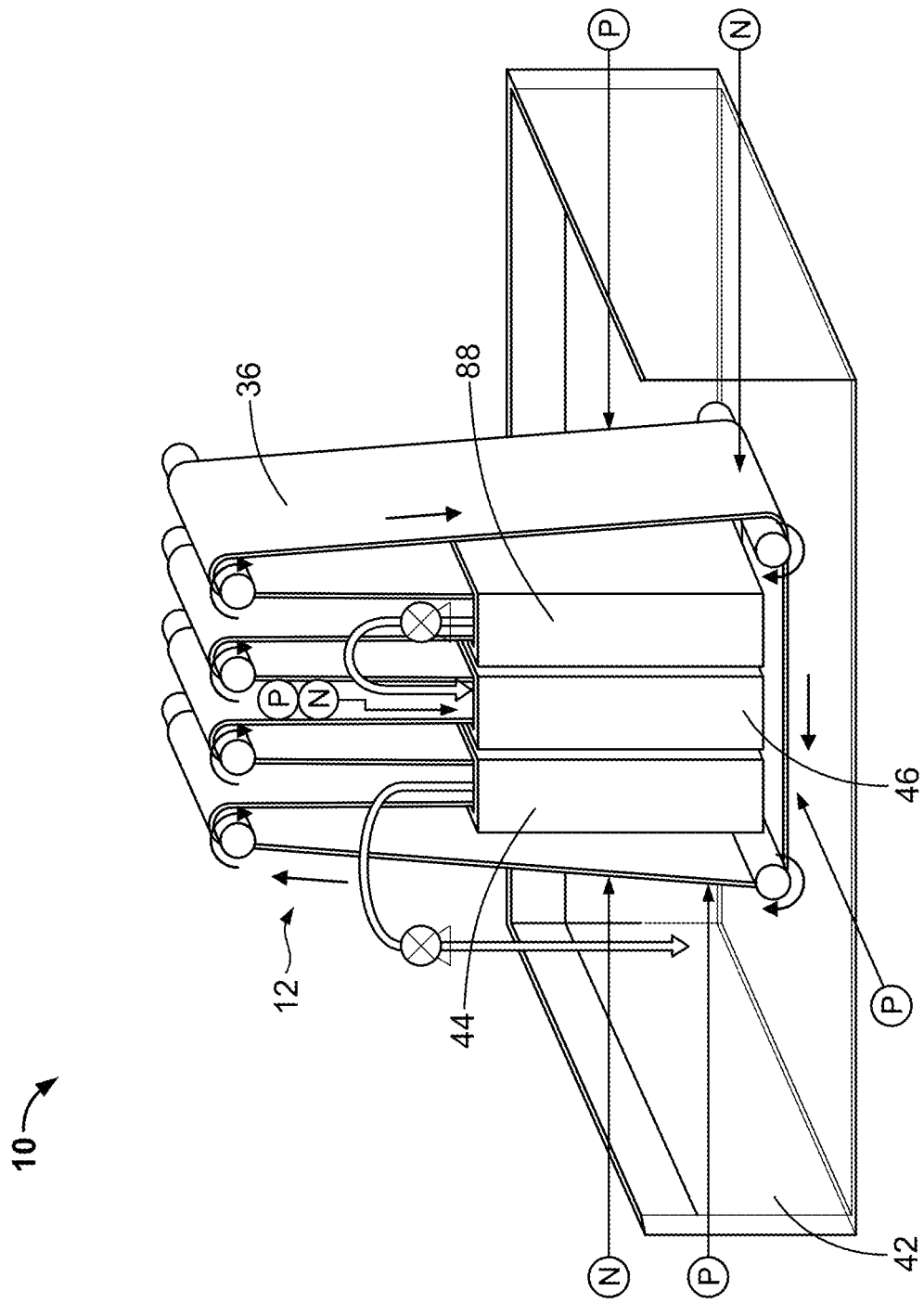
FIG. 37 depicts a perspective view of a system which utilizes microorganisms for removing a pollutant from a fluid according to one embodiment; wherein the system comprises four reservoirs.

In the following detailed description of the embodiments, reference is made to the accompanying drawings which form a part hereof, and in which is shown by way of illustration specific embodiments in which the disclosure may be practiced. The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure. It will be understood by those skilled in the art that various changes in form and details may be made without departing from the principles and scope of the disclosure. It is intended to cover various modifications and similar arrangements and procedures, and the scope of the appended claims therefore should be accorded the broadest interpretation so as to encompass all such modifications and similar arrangements and procedures.

Although this disclosure has been described relative to specific materials, it is not limited to the specific materials or apparatuses but only to their specific characteristics and capabilities and other materials and apparatuses can be substituted as is well understood by those skilled in the art after appreciating the present disclosure.

It is to be understood that the terms such as left, right, top, bottom, front, back, side, height, length, width, upper, lower, interior, exterior, inner, outer, and the like as may be used herein, merely describe points of reference and do not limit the present disclosure to any particular orientation or configuration.

As used herein, the term "or" includes one or more of the associated listed items, such that "A or B" means "A but not B," and "B but not A". As used herein, the term "and" includes all combinations of one or more of the associated listed items, such that "A and B" means "A as well as B". The use of "and/or" includes all combinations of one or more of the associated listed items, such that "A and/or B" includes "A but not B," "B but not A," and "A as well as B," unless it is clearly indicated that only a single item, subgroup of items, or all items are present. The use of "etc." is defined as "et cetera" and indicates the inclusion of all other elements belonging to the same group of the preceding items, in any "and/or" combination(s).

As used herein, the singular forms "a," "an," and "the" are intended to include both the singular and plural forms, unless the language explicitly indicates otherwise. Indefinite articles like "a" and "an" introduce or refer to any modified term, both previously-introduced and not, while definite articles like "the" refer to a same previously-introduced term; as such, it is understood that "a" or "an" modify items that are permitted to be previously-introduced or new, while definite articles modify an item that is the same as immediately previously presented. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

It will be understood that when an element is referred to as being "connected," "coupled," "mated," "attached," "fixed," etc. to another element, it can be directly connected to the other element, or intervening elements may be present. In contrast, when an element is referred to as being "directly connected," "directly coupled," etc. to another element, there are no intervening elements present. Other words used to describe the relationship between elements should be interpreted in a like fashion (e.g., "between" versus "directly between," "adjacent" versus "directly adjacent," etc.). Similarly, a term such as "communicatively connected" includes all variations of information exchange and routing between two electronic devices, including intermediary devices, networks, etc., connected wirelessly or not.

It will be understood that, although the ordinal terms "first," "second," etc. may be used herein to describe various elements, these elements should not be limited to any order by these terms. These terms are used only to distinguish one element from another; where there are "second" or higher ordinals, there merely must be that many number of elements, without necessarily any difference or other relationship. For example, a first element could be termed a second element, and, similarly, a second element could be termed a first element, without departing from the scope of example embodiments or methods.

Similarly, the structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

A Method of Facilitating or Inhibiting Growth of Specific Microorganisms Wherein Microorganisms Uptake and Release Pollutants In the arrangement shown, as one example, a system or method of using microorganisms 84 such as bacteria, algae 52, and the like to remove a pollutant 56 from a fluid 58 (or simply "system" 10) is formed of any suitable size, shape, and design and is configured to be utilized in association with any type of microorganism growing apparatus 12. In one arrangement, as shown, the system 10 comprises a microorganism growing apparatus 12, microorganisms 84, and a first fluid 58 (or simply "a fluid" 58) wherein the microorganisms 84 remove a pollutant 56 from the fluid 58.

In one arrangement, as one example, the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; filling the second reservoir 44 with a second fluid 60; controlling the second fluid 60 within the second reservoir 44 to have a second condition 66; growing microorganisms 84 using the microorganism growing apparatus 12; exposing the microorganisms 84 to the first fluid 58 within the first reservoir 42 wherein the microorganisms 84 are exposed to the first condition 64 and the microorganisms 84 uptake the pollutant 56 from the first fluid 58; exposing the microorganisms 84 to light 50 and air 48; and exposing the microorganisms 84 to the second fluid 60 within the second reservoir 44 wherein the microorganisms 84 are exposed to the second condition 66 and the microorganisms 84 are stimulated to release the pollutant 56. Furthermore, this arrangement of the system 10 may also comprise the steps of: providing a third reservoir 46; filling the third reservoir 46 with a third fluid 62; controlling the third fluid 62 within the third reservoir 46 to have a third condition 68; and submerging a portion of the microorganisms 84 within the third fluid 62 of the third reservoir 46 thereby exposing this portion of the microorganisms 84 to the third condition 68. Any number of reservoirs 42/44/46 are hereby contemplated for use.

In another arrangement, the system 10 comprises the steps of: providing a microorganism growing apparatus 12 having a first reservoir 42, a second reservoir 44, and at least one moving belt 36; filling the first reservoir 42 with a first fluid 58 that has a high concentration of the pollutant 56; controlling the first fluid 58 within the first reservoir 42 to have a first condition 64; filling the second reservoir 44 with a second fluid 60; controlling the second fluid 60 within the second reservoir 44 to have a second condition 66; moving the at least one belt 36 between a first submerged position 70, wherein a portion of the at least one belt 36 is submerged within the first fluid 58 held within the first reservoir 42, and an exposed position 76, wherein a portion of the at least one belt 36 is not submerged within the first fluid 58 held within the first reservoir 42; moving the portion of the at least one belt 36 to the exposed position wherein this portion of the at least one belt 36 is exposed to air 48 and light 50; growing microorganisms 84 on the at least one belt 36 as the at least one belt 36 moves through the microorganism growing apparatus 12, wherein the microorganisms 84 consume the pollutant 56 from the first fluid 58 held within the first reservoir 42 during the growing process; moving the at least one belt 36 to a second submerged position 72, wherein a portion of the at least one belt 36 is submerged within the second fluid 60 of the second reservoir 44 thereby exposing this portion of the at least one belt 36 to the second condition 66 thereby stimulating the microorganisms 84 contained on this portion of the belt 36 to release the pollutant 56. Additionally, this arrangement of the system 10 may further comprise the steps of: providing a third reservoir 46; filling the third reservoir 46 with a third fluid 62; controlling the third fluid 62 within the third reservoir 46 to have a third condition 68; and submerging a portion of the microorganisms 84 within the third fluid 62 of the third reservoir 46 thereby exposing this portion of the microorganisms 84 to the third condition 68.

In one arrangement, as one example, the system 10 comprises the steps of: providing microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; filling the second reservoir 44 with a second fluid 60; controlling the second fluid 60 within the second reservoir 44 to have a second condition 66; growing an algae biofilm 54 using the microorganism growing apparatus 12; moving the algae biofilm 54 to a first submerged position 70 such that a portion of the algae biofilm 54 is submerged within the first fluid 58 held within the first reservoir 42 exposing the algae biofilm 54 to the first condition 64 wherein the algae 52 uptakes the pollutant 56 from the first fluid 58 held within the first reservoir 42; moving the algae biofilm 54 such that it is exposed to air 48 and light 50; following the uptake of the pollutant 56, moving the algae biofilm 54 to a second submerged position 72 such that a portion of the algae biofilm 54 is submerged within the second fluid 60 held within the second reservoir 44 exposing the algae biofilm 54 to the second condition 66 and stimulating the algae biofilm 54 to release the pollutant 56. Furthermore, this arrangement of the system 10 may also comprise the steps of: providing a third reservoir 46; filling the third reservoir 46 with a third fluid 62; controlling the third fluid 62 within the third reservoir 46 to have a third condition 68; and moving the algae biofilm 54 to a third submerged position 74 such that a portion of the algae biofilm 54 is submerged within the third fluid 62 of the third reservoir 46 thereby exposing this portion of the algae biofilm 54 to the third condition 68.

In another arrangement, the system 10 comprises the steps of: providing a microorganism growing apparatus 12 having a first reservoir 42, a second reservoir 44, and at least one moving belt 36; filling the first reservoir 42 with a first fluid 58 that has a high concentration of the pollutant 56; controlling the first fluid 58 within the first reservoir 42 to have a first condition 64; filling the second reservoir 44 with a second fluid 60; controlling the second fluid 60 within the second reservoir 44 to have a second condition 66; moving the at least one belt 36 between a first submerged position 70, wherein a portion of the at least one belt 36 is submerged within the first fluid 58 held within the first reservoir 42, and an exposed position 76, wherein a portion of the at least one belt 36 is not submerged within the first fluid 58 held within the first reservoir 42; moving the portion of the at least one belt 36 to the exposed position wherein this portion of the at least one belt 36 is exposed to air 48 and light 50; growing an algae biofilm 54 on the at least one belt 36 as the at least one belt 36 moves through the microorganism growing apparatus 12, wherein the algae 52 consumes the pollutant 56 from the first fluid 58 held within the first reservoir 42 during the growing process; moving the at least one belt 36 to a second submerged position 72, wherein a portion of the at least one belt 36 is submerged within the second fluid 60 of the second reservoir 44 thereby exposing this portion of the at least one belt 36 to the second condition 66 thereby stimulating the algae 52 contained on this portion of the belt 36 to release the pollutant 56. Additionally, this arrangement of the system 10 may further comprise the steps of: providing a third reservoir 46; filling the third reservoir 46 with a third fluid 62; controlling the third fluid 62 within the third reservoir 46 to have a third condition 68; and submerging a portion of the algae biofilm 54 within the third fluid 62 of the third reservoir 46 thereby exposing this portion of the algae biofilm 54 to the third condition 68.

Additionally, in another arrangement, the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; allowing the second reservoir 44 to not contain a fluid either by not filling the second reservoir 44 with a fluid or draining the second reservoir 44 of the fluid contained therein;

controlling the second reservoir 44 to have a second condition 66; growing microorganisms 84 using the microorganism growing apparatus 12; exposing the microorganisms 84 to the first fluid 58 within the first reservoir 42 wherein the microorganisms 84 are exposed to the first condition 64 and the microorganisms 84 uptake the pollutant 56 from the first fluid 58; exposing the microorganisms 84 to light 50 and air 48; and exposing the microorganisms 84 to the second reservoir 44 wherein the microorganisms 84 are exposed to the second condition 66 and the microorganisms 84 are stimulated to release the pollutant 56. Furthermore, this arrangement of the system 10 may also comprise the steps of: providing a third reservoir 46 wherein the third reservoir 46 may be filled with a fluid 62 and the fluid 62 is controlled to have a third condition 68 and a portion of the microorganisms 84 are submerged within the fluid 62 of the third reservoir 46 thereby exposing this portion of the microorganisms 84 to the third condition 68. Any number of reservoirs 42/44/46/88 are hereby contemplated for use and any of the reservoirs 42/44/46/88 may be filled with a fluid 58/60/62 or left dry/empty and then manipulated to have a condition 64/66/68 utilized to stimulate the microorganisms 84.

In another arrangement of the system 10 the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; allowing the second reservoir 44 to not contain a fluid either by not filling the second reservoir 44 with a fluid or draining the second reservoir 44 of the fluid contained therein; controlling the second reservoir 44 to have a second condition 66; growing microorganisms 84 using the microorganism growing apparatus 12; exposing the microorganisms 84 to the first fluid 58 within the first reservoir 42 wherein the microorganisms 84 are exposed to the first condition 64 and the microorganisms 84 uptake the pollutant 56 from the first fluid 58; exposing the microorganisms 84 to light 50 and air 48; and exposing the microorganisms 84 to the second reservoir 44 wherein the microorganisms 84 are exposed to the second condition 66; providing a third reservoir 46 wherein the third reservoir 46 is not filled with a fluid, but instead the third reservoir 46 is dry/empty and is controlled to have a third condition 68 and the microorganisms 84 are exposed to the third condition 68. Any number of reservoirs 42/44/46/88 are hereby contemplated for use and any of the reservoirs 42/44/46/88 may be filled with a fluid, left dry/empty, or drained of the fluid to become dry/empty and then manipulated to have a condition 64/66/68 utilized to stimulate the microorganisms 84.

In another arrangement, as one example, the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; filling the second reservoir 44 with a second fluid 60; controlling the second fluid 60 within the second reservoir 44 to have a second condition 66; growing microorganisms 84 using the microorganism growing apparatus 12; exposing the microorganisms 84 to the first fluid 58 within the first reservoir 42 wherein the microorganisms 84 are exposed to the first condition 64 and the microorganisms 84 uptake the pollutant 56 from the first fluid 58; exposing the microorganisms 84 to light 50 and air 48; and exposing the microorganisms 84 to the second fluid 60 within the second reservoir 44 wherein the microorganisms 84 are exposed to the second condition 66 and the microorganisms 84 are stimulated to release the pollutant 56. Additionally, this arrangement of the system 10 may also comprise the steps of: providing a third reservoir 46; filling the third reservoir 46 with a third fluid 62; controlling the third fluid 62 within the third reservoir 46 to have a third condition 68; and submerging a portion of the microorganisms 84 within the third fluid 62 of the third reservoir 46 thereby exposing this portion of the microorganisms 84 to the third condition 68. Any number of reservoirs 42/44/46 are hereby contemplated for use. Furthermore, the first condition 64, the second condition 66, and/or the third condition 68, etc. may facilitate or inhibit growth of one or more specific types of microorganism 84. In one arrangement, as one example, the first condition 64, the second condition 66, and/or the third condition 68 facilitates growth of one or more desirable species of microorganisms 84 or a desirable consortium of microorganisms 84. The desirable species may include, for example, *Chlorella* algae 78 or *Spirulina* algae 80. In another arrangement, as one example, the first condition 64, the second condition 66, and/or the third condition 68 inhibits growth of an undesirable species of microorganisms 84 or an undesirable consortium of microorganisms 84. The undesirable species may include, for example, *Chlorella* algae 78 or *Spirulina* algae 80. The specific type of microorganism or consortium may include *Chlorella, Spirulina, Chlamydomonas, Dunaliella, Picochlorum, Botryococcus, Phaeodactylum, Thalassiosira, Nannochloropsis, Isochrysis, Scenedesmus, Anabaena, Nostoc, Arthrospira, Microcoleus*, Achnanthidium, *Ulnaria*, or a combination thereof. In some embodiments, the consortium of microorganisms includes at least two of bacteria, fungi, or algae. The ability to facilitate or inhibit growth of a specific species of microorganism 84 allows the system 10 to function more effectively and efficiently.

Microorganisms

The system 10 is capable of using microorganisms 84 to remove a pollutant 56 from a fluid 58. Any type of microorganism 84 may be utilized in the system 10 without departing from the scope of the disclosure. In one arrangement, as one example, the microorganisms 84 may be bacteria or algae 52. Additionally, in one arrangement, the microorganisms 84 may be fungi.

In one arrangement, as one example, the system 10 uses microorganisms 84 to remove a pollutant 56 from a fluid 58 by providing microorganism growing apparatus 12 having a first reservoir 42 and a second reservoir 44, filling the first reservoir 42 with a first fluid 58 that contains a pollutant 56, controlling the first fluid 58 within the first reservoir 42 to have a first condition 64, filling the second reservoir 44 with a second fluid 60, controlling the second fluid 60 within the second reservoir 44 to have a second condition 66, growing the microorganisms 84 using the microorganism growing apparatus 12, exposing the microorganisms 84 to the first fluid 58 within the first reservoir 42 wherein the microorganisms 84 is exposed to the first condition 64 and the microorganisms 84 uptake the pollutant 56 from the first fluid 58, exposing the microorganisms 84 to light 50 and air 48, and exposing the microorganisms 84 to the second fluid 60 within the second reservoir 44 wherein the microorganisms 84 are exposed to the second condition 66 and the microorganisms 84 is stimulated to release the pollutant 56.

In another arrangement, the first condition 64, the second condition 66, and/or the third condition 68 facilitates or inhibits growth of a specific species of microorganism 84. In one arrangement, as one example, the system 10 uses microorganisms 84 to remove a pollutant 56 from a fluid 58 by providing microorganism growing apparatus 12 having a first reservoir 42 and a second reservoir 44, filling the first reservoir 42 with a first fluid 58 that contains a pollutant 56, controlling the first fluid 58 within the first reservoir 42 to have a first condition 64, filling the second reservoir 44 with a second fluid 60, controlling the second fluid 60 within the second reservoir 44 to have a second condition 66, growing the microorganisms 84 using the microorganism growing apparatus 12, exposing the microorganisms 84 to the first fluid 58 within the first reservoir 42 wherein the microorganisms 84 is exposed to the first condition 64 and the microorganisms 84 uptake the pollutant 56 from the first fluid 58, exposing the microorganisms 84 to light 50 and air 48, and exposing the microorganisms 84 to the second fluid 60 within the second reservoir 44 wherein the microorganisms 84 are exposed to the second condition 66, which facilitates or inhibits growth of a specific species of microorganisms 84 and stimulates the microorganisms 84 to release the pollutant 56. The specific type of microorganism or consortium may include *Chlorella, Spirulina, Chlamydomonas, Dunaliella, Picochlorum, Botryococcus, Phaeodactylum, Thalassiosira, Nannochloropsis, Isochrysis, Scenedesmus, Anabaena, Nostoc, Arthrospira, Microcoleus,* Achnanthidium, *Ulnaria,* or a combination thereof. In some embodiments, the consortium of microorganisms includes at least two of bacteria, fungi, or algae.

Algae

The system 10 is capable of using algae 52 as the microorganism 84 to remove a pollutant 56 from a fluid 58 by providing a microorganism growing apparatus 12 having a first reservoir 42 and a second reservoir 44, filling the first reservoir 42 with a first fluid 58 that contains a pollutant 56, controlling the first fluid 58 within the first reservoir 42 to have a first condition 64, filling the second reservoir 44 with a second fluid 60, controlling the second fluid 60 within the second reservoir 44 to have a second condition 66, growing algae 52 using the microorganism growing apparatus 12, exposing the algae 52 to the first fluid 58 within the first reservoir 42 wherein the algae 52 is exposed to the first condition 64 and the algae 52 uptakes the pollutant 56 from the first fluid 58, exposing the algae 52 to light 50 and air 48, and exposing the algae 52 to the second fluid 60 within the second reservoir 44 wherein the algae 52 is exposed to the second condition 66 and the algae 52 is stimulated to release the pollutant 56.

Any species or type of algae 52 may be utilized in the system 10 without departing from the scope of the disclosure. In one arrangement, as one example, the algae 52 may be *Chlorella* algae 78 or *Spirulina* algae 80. Additionally, in one arrangement, the algae 52 may be of the type regarded as Generally Regarded As Safe.

As stated above, any type of algae 52 may be utilized in the system 10. In one arrangement, as one example, biofilm based algae 54 ("an algae biofilm" 54) may be utilized. Alternatively, in another arrangement, as one example, suspended algal culture systems may also be utilized without departing from the scope of the disclosure.

In one arrangement, as one example, the algae 52 contains extracellular polymeric substances which enhance absorption of pollutants 56, including, but not limited to, phosphorous, by the algae 52. Additionally, in one arrangement, the algae 52 contains extracellular polymeric substances which protect the algae 52 from toxic effects of high concentrations of pollutants 56, such as phosphorous.

In one arrangement, as one example, the first condition 64, the second condition 66, and/or the third condition 68 facilitates growth of a desirable species of microorganisms 84 or a desirable consortium of microorganisms 84 such as *Chlorella* algae 78 or *Spirulina* algae 80. In another arrangement, as one example, the first condition 64, the second condition 66, and/or the third condition 68 inhibits growth of a specific type of microorganism 84 such as *Chlorella* algae 78 or *Spirulina* algae 80.

Pollutant

The system 10 provides a method of using microorganisms 84 to remove a pollutant 56, from a fluid 58. Any type of pollutant 56 may be removed from the fluid 58 without departing from the scope of the disclosure. In one arrangement, as one example, the pollutant 56 is Nitrogen (N), Phosphorous (P), Potassium (K), Carbon (C), toxic metals, salts, pharmaceuticals, or hormones. In another arrangement, the pollutant 56 is a PPCPs (Pharmaceuticals and Personal Care Products) wherein the pollutant 56 is any type of PPCPs without departing from the scope of the disclosure. For example, the pollutant 56 may be one or more of the following PPCPs: caffeine, Carbamazepine, Gemfribrozil, Ibuprofen, Naproxen, Sulfamethoxazole, Triclosan, and the like.

In one arrangement, as one example, the system 10 provides a method of using microorganisms 84 to remove phosphorous from a fluid 58, the steps comprising: providing a microorganism growing apparatus 12 having a first reservoir 42 and a second reservoir 44, filling the first reservoir 42 with a first fluid 58 that contains phosphorous, controlling the first fluid 58 within the first reservoir 42 to have a first condition 64, filling the second reservoir 44 with a second fluid 60, controlling the second fluid 60 within the second reservoir 44 to have a second condition 66, growing microorganisms 84 using the microorganism growing apparatus 12, exposing the microorganisms 84 to the first fluid 58 within the first reservoir 42 wherein the microorganisms 84 is exposed to the first condition 64 and the microorganisms 84 uptake the phosphorous from the first fluid 58, exposing the microorganisms 84 to light 50 and air 48, and exposing the microorganisms 84 to the second fluid 60 within the second reservoir 44 wherein the microorganisms 84 is exposed to the second condition 66 and the microorganisms 84 is stimulated to release the phosphorous.

Microorganism Growing Apparatus

As provided above, system 10 may utilize a microorganism growing apparatus 12. Microorganism growing apparatus 12 is formed of any suitable size, shape, and design and is configured to grow any type of microorganism 84 including, but not limited to, algae 52. The microorganism growing apparatus 12 is configured to grow microorganisms 84 in any form without departing from the scope of the disclosure. In one arrangement, as one example, the microorganism growing apparatus 12 is configured to grow algae 52 in a biofilm 54. In one arrangement, as one example, the microorganism growing apparatus 12 is configured to grow algae 52 in a biofilm 54 wherein the algae biofilm 54 is grown on the at least one moving belt 36. In the arrangement shown, as one example, for purposes of clarity, the microorganism growing apparatus 12 has a front 14, a back 16, opposing sides 18, a top 20, and a bottom 22. In the arrangement shown, as one example, the microorganism growing apparatus 12 is symmetrical, or generally symmetrical, or operatively symmetrical, and for this reason, unless specified otherwise, description of one side 18 of the microorganism growing apparatus 12 shall apply to both sides 18 of the microorganism growing apparatus 12 which is separated by an imaginary centerline that extends down the approximate top-to-bottom center of the microorganism growing apparatus 12. Further description of a microorganism growing apparatus can be found in U.S. Pat. No. 9,932,549, which is hereby incorporated by reference in its entirety.

In the arrangement shown, as one example, the microorganism growing apparatus 12 is formed of a frame 24, a motor 26, at least one drive shaft 28, a gear system 30, a plurality of rollers 32, a mechanized harvesting system 34, which comprises at least one moving belt 36, a harvesting blade 38, a harvesting reservoir 40. Also, the microorganism growing apparatus 12 is formed of a first reservoir 42, a first fluid 58, a $CO_2$-rich gaseous phase 48 (also referred to as "air" throughout the disclosure), and light 50 (also referred to as a "sunlight capture" part throughout the disclosure). Furthermore, the microorganism growing apparatus 12 may also include additional components, such as, a pump 82. Any type or form of microorganism growing apparatus 12 may be utilized in the system 10, including, but not limited to, horizontal stationary sheets with microorganisms 84 growing on the surface, vertical stationary sheets with microorganisms 84 growing on the surface, rotating drums with microorganisms 84 growing on the surface, small floating beads and/or solid media with microorganisms 84 growing on their surface without departing from the scope of the disclosure.

In one arrangement, as shown, the microorganism growing apparatus 12 comprises a plurality of reservoirs 42/44/46/88. For example, in one arrangement, the microorganism growing apparatus 12 comprises a first reservoir 42 and a second reservoir 44. In another arrangement, as shown, the microorganism growing apparatus 12 comprises a first reservoir 42, a second reservoir 44, and a third reservoir 46. Any type or form of reservoirs 42/44/46/88 may be utilized in the microorganism growing apparatus 12 without departing from the scope of the disclosure. Any number of reservoirs 42/44/46/88 may be utilized in the microorganism growing apparatus 12 without departing from the scope of the disclosure.

Frame

As provided above, the microorganism growing apparatus 12 comprises a frame 24, among other components. Frame 24 is formed of any suitable size, shape, and design and is configured to support the microorganism growing apparatus 12 and allow the microorganism growing apparatus 12 to remain in an upright position in order to operate. In one arrangement, frame is square or rectangular in shape. However, any other shape or configuration is hereby contemplated for use. The frame 24 may be configured to be any size without departing from the disclosure. The frame 24 may be manufactured to be small enough to fit on a shelf for research purposes and the like or large enough to serve a large metropolitan city. Furthermore, frame 24 may be formed of any material including, but not limited to, plastic, metal, non-metal material, and PVC.

Frame 24 provides the structure of the microorganism growing apparatus 12. In one arrangement, as shown, the at least one moving belt 36 is supported by frame 24. In one arrangement, the at least one drive shaft 28 is coupled with the frame 24 wherein the at least one drive shaft 28 supports and actuates the at least one moving belt 36. In one arrangement, as one example, the microorganism growing apparatus 12 comprises a gear system 30 wherein the gear system 30 is coupled with the at least one drive shaft 28, a plurality of rollers 32 wherein the plurality of rollers 32 is coupled with the frame 24 which guides the at least one moving belt 36.

Reservoir

As stated above, the microorganism growing apparatus 12 comprises at least one reservoir 42/44/46, among other components. Reservoir 42/44/46 is formed of any suitable size, shape, and design and is configured to support the microorganism growing apparatus 12 and contain a fluid 58/60/62. In one arrangement, as one example, reservoir 42/44/46 is circular, square, or rectangular in shape. However, any other shape or configuration is hereby contemplated for use. Furthermore, the reservoir 42/44/46, and the microorganism growing apparatus 12, may be any size without departing from the disclosure. The reservoir 42/44/46, and the microorganism growing apparatus 12, may be manufactured to be small enough to fit on a shelf for research purposes and the like, or large enough to efficiently and effectively serve a large metropolitan city. Reservoir 42/44/46 may be formed of any type of reservoir 42/44/46 configured to contain fluid 58/60/62 including, but not limited to, a trough system 86.

In one arrangement, as shown the microorganism growing apparatus 12 comprises a first reservoir 42, among other components. In another arrangement, as shown, the microorganism growing apparatus 12 comprises a first reservoir 42 and a second reservoir 44, among other components. In another arrangement, as shown, the microorganism growing apparatus 12 comprises a first reservoir 42, a second reservoir 44, and a third reservoir 46. Any number of reservoirs 42/44/46/88 may be utilized by the system 10 without departing from the scope of the disclosure. For example, the microorganism growing apparatus 12 may comprise one, two, three, four, five, six, seven, eight, nine, ten, or more reservoirs 42/44/46/88 without departing from the scope of the disclosure. Throughout the disclosure, reference to a reservoir 42/44/46/88 refers to a first reservoir 42, a second reservoir 44, a third reservoir 46, or a fourth reservoir 88; unless the disclosure specifically states that it is referring to only one of the reservoirs 42/44/46/88.

In one arrangement, as one example, the system 10 comprises a microorganism growing apparatus 12 having a first reservoir 42 and a second reservoir 44 wherein the first reservoir 42 is filled with a first fluid 58 that contains a pollutant 56, the first fluid 58 is controlled to have a first condition 64, the second reservoir 44 is filled with a second fluid 60, the second fluid 60 is controlled to have a second condition 66, microorganisms 84 are grown using the microorganism growing apparatus 12, the microorganisms 84 are exposed to the first fluid 58 wherein the microorganisms 84 are exposed to the first condition 64 and the microorganisms 84 uptake the pollutant 56 from the first fluid 58, the microorganisms 84 are exposed to light 50 and air 48 and the microorganisms 84 are exposed to the second fluid 60 wherein the microorganisms 84 are exposed to the second condition 66 and the microorganisms 84 are stimulated to release the pollutant 56.

In another arrangement, for example, the system 10 comprises a microorganism growing apparatus 12 having a first reservoir 42 and a second reservoir 44 wherein the first reservoir 42 is filled with a first fluid 58 that contains a pollutant 56, the first fluid 58 is controlled to have a first condition 64, the second reservoir 44 is filled with a second fluid 60, the second fluid 60 is controlled to have a second condition 66, microorganisms 84 are grown using the microorganism growing apparatus 12, the microorganisms 84 are exposed to the first fluid 58 wherein the microorganisms 84 are exposed to the first condition 64 and the microorganisms 84 uptake the pollutant 56 from the first fluid 58, microorganisms 84 are exposed to light 50 and air 48 and the microorganisms 84 are exposed to the second fluid 60 wherein the microorganisms 84 are exposed to the second condition 66 and the microorganisms 84 are stimulated to release the pollutant 56.

Furthermore, in an alternative arrangement, the system 10 comprises a microorganism growing apparatus 12 having a first reservoir 42 and a second reservoir 44 wherein the first reservoir 42 is filled with a first fluid 58 that contains a pollutant 56, the first fluid 58 is controlled to have a first condition 64, the second reservoir 44 is filled with a second fluid 60, the second fluid 60 is controlled to have a second condition 66, algae 52 is grown using the microorganism growing apparatus 12, the algae 52 is exposed to the first fluid 58 wherein the algae 52 is exposed to the first condition 64 and the algae 52 uptakes the pollutant 56 from the first fluid 58, the algae 52 is exposed to light 50 and air 48 and the algae 52 is exposed to the second fluid 60 wherein the algae 52 is exposed to the second condition 66 and the algae 52 is stimulated to release the pollutant 56, then a third reservoir 46 is provided, the third reservoir 46 is filled with a third fluid 62, the third fluid 62 is controlled within the third reservoir 46 to have a third condition 68, and a portion of the algae biofilm 54 is submerged within the third fluid 62 of the third reservoir 46 thereby exposing this portion of the algae biofilm 54 to the third condition 68 in order to stimulate the algae 52 to release the pollutant 56.

In one arrangement, as shown, the first reservoir 42 is located at the bottom 22 of the microorganism growing apparatus 12. The first reservoir 42 is designed to contain or hold the first fluid 58 which contains a pollutant 56. In one arrangement, as one example, the at least one moving belt 36 is moved through the microorganism growing apparatus 12 wherein a portion of the at least one moving belt 36 is in a first submerged position 70 wherein a portion of the at least one moving belt 36 is submerged within the first fluid 58 held within the first reservoir 42 and the microorganisms 84 on the at least one moving belt 36 are exposed to a first condition 64 within the first fluid 58 wherein the microorganisms 84 uptake the pollutant 56 from the first fluid 58. Then the at least one moving belt 36 transitions to an exposed position 76 wherein a portion of the at least one moving belt 36 is not submerged within the first fluid 58 held within the first reservoir 42, but is exposed to air 48 and light 50.

In another arrangement, as shown, the microorganism growing apparatus 12 comprises a first reservoir 42 and a second reservoir 44 wherein the first reservoir 42 is located at the bottom 22 of the microorganism growing apparatus 12 and the first reservoir 42 is designed to contain or hold the first fluid 58. Additionally, the second reservoir 44 is located within or near the first reservoir 42 and the second reservoir 44 is designed to contain or hold the second fluid 60. In this arrangement, as one example, the at least one moving belt 36 is moved through the microorganism growing apparatus 12 wherein a portion of the at least one moving belt 36 is in a first submerged position 70 wherein the at least one moving belt 36 is submerged within the first fluid 58 held within the first reservoir 42, then to an exposed position 76 wherein a portion of the at least one moving belt 36 is not submerged within the first fluid 58 held within the first reservoir 42, but is exposed to air 48 and light 50. Then the at least one moving belt 36 is in a second submerged position 72 wherein the at least one moving belt 36 is submerged within the second fluid 60 held within the second reservoir 44 wherein the microorganisms 84 are exposed to a second condition 66 within the second fluid 60 and the microorganisms 84 are stimulated to release a pollutant 56.

In one arrangement, as another example, the microorganism growing apparatus 12 comprises a first reservoir 42, a second reservoir 44, and a third reservoir 46 wherein the first reservoir 42 is located at the bottom 22 of the microorganism growing apparatus 12 and the first reservoir 42 is designed to contain or hold the first fluid 58 which contains a pollutant 56. Additionally, the second reservoir 44 and the third reservoir 46 are located within or near the first reservoir 42 and the second reservoir 44 is designed to contain or hold the second fluid 60 and the third reservoir 46 is designed to contain or hold the third fluid 62. In this arrangement, as one example, the at least one moving belt 36 is moved through the microorganism growing apparatus 12 wherein a portion of the at least one moving belt 36 is in a first submerged position 70 wherein the at least one moving belt 36 is submerged within the first fluid 58 held within the first reservoir 42 and the microorganisms 84 on the at least one moving belt 36 are exposed to a first condition 64 wherein the microorganisms 84 uptake the pollutant 56 from the first fluid 58, then to an exposed position 76 wherein a portion of the at least one moving belt 36 is not submerged within the first fluid 58 held within the first reservoir 42, but is exposed to air 48 and light 50. Then, the at least one moving belt 36 is in a second submerged position 72 wherein a portion of the at least one moving belt 36 is submerged within the second fluid 60 held within the second reservoir 44 wherein the microorganisms 84 on the at least one moving belt 36 are exposed to a second condition 66 within the second fluid 60 and the microorganisms 84 are stimulated to release the pollutant 56. Furthermore, the at least one moving belt 36 is in a third submerged position 74 wherein a portion of the at least one moving belt 36 is submerged within the third fluid 62 held within the third reservoir 46 wherein the microorganisms 84 on the at least one moving belt 36 are exposed to a third condition 68 within the third fluid 62 and the microorganisms 84 are stimulated to release the pollutant 56.

In one arrangement, as one example, reservoir 42/44/46 may also include a pump 82 which is configured to circulate fluid 58/60/62 within reservoir 42/44/46. The circulation of the fluid 58/60/62 within reservoir 42/44/46 may improve the growth of the microorganisms 84 and the efficiency of the system 10. As described in more detail below, pump 82 may be any type of pump 82 such as a paddlewheel.

Additionally, it is important to note, while the system 10 may comprise any number of reservoirs 42/44/46, the at least one moving belt 36 is not required to be submerged within each reservoir 42/44/46. For example, in one arrangement, the microorganism growing apparatus 12 comprises a first reservoir 42, a second reservoir 44, and a third reservoir 46 wherein the first reservoir 42 is located at the bottom 22 of the microorganism growing apparatus 12 and the first reservoir 42 is designed to contain or hold the first fluid 58 which contains a pollutant 56. Additionally, the second reservoir 44 and the third reservoir 46 are located within or near the first reservoir 42 and the second reservoir 44 is designed to contain or hold the second fluid 60 and the third reservoir 46 is designed to contain or hold the third fluid 62. In this arrangement, as one example, the at least one moving belt 36 is moved through the microorganism growing apparatus 12 wherein a portion of the at least one moving belt 36 is in a first submerged position 70 wherein the at least one moving belt 36 is submerged within the first fluid 58 held within the first reservoir 42 and the microorganisms 84 on the at least one moving belt 36 is exposed to a first condition 64 wherein the microorganisms 84 uptake the pollutant 56 from the first fluid 58, then to an exposed position 76 wherein a portion of the at least one moving belt 36 is not submerged within the first fluid 58 held within the first reservoir 42, but is exposed to air 48 and light 50. Then, the at least one moving belt 36 skips over the second reservoir 44 bypassing the second submerged position 72 wherein the at least one moving belt 36 is not submerged within the second fluid 60. Instead, the at least one moving belt 36 moves to a third submerged position 74 wherein a portion of the at least one moving belt 36 is submerged within the third fluid 62 held within the third reservoir 46 wherein the algae 52 on the at least one moving belt 36 is exposed to a third condition 68 within the third fluid 62 and the microorganisms 84 are stimulated to release the pollutant 56.

Furthermore, while a reservoir 42/44/46/88 may be filled with a fluid 58/60/62, in an alternative arrangement, any reservoir 42/44/46/88 may be left dry/empty or drained of the fluid 58/60/62 in order to become dry/empty. Also, a dry/empty reservoir 42/44/46/88 may still have a condition in order to stimulate the microorganisms 84.

Therefore, in an alternative arrangement, the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; allowing the second reservoir 44 to remain dry/empty by not filling the second reservoir 44 with a fluid or by draining the second reservoir 44 of the fluid contained therein; controlling the second reservoir 44 to have a second condition 66; growing microorganisms 84 using the microorganism growing apparatus 12; exposing the microorganisms 84 to the first fluid 58 within the first reservoir 42 wherein the microorganisms 84 are exposed to the first condition 64 and the microorganisms 84 uptake the pollutant 56 from the first fluid 58; exposing the microorganisms 84 to light 50 and air 48; and exposing the microorganisms 84 to the second reservoir 44 wherein the microorganisms 84 are exposed to the second condition 66 and the microorganisms 84 are stimulated to release the pollutant 56. This arrangement of the system 10 may also comprise the steps of: providing a third reservoir 46 wherein the third reservoir 46 may be filled with a fluid 62 and the fluid 62 is controlled to have a third condition 68 and a portion of the microorganisms 84 are submerged within the fluid 62 of the third reservoir 46 thereby exposing this portion of the microorganisms 84 to the third condition 68. Any number of reservoirs 42/44/46/88 are hereby contemplated for use and any of the reservoirs 42/44/46/88 may be filled with a fluid 58/60/62 or left dry/empty and then manipulated to have a condition 64/66/68 utilized to stimulate the microorganisms 84. In one arrangement, one or more of the reservoirs 42/44/46/88 may be dry/empty and contain infrared heat as the condition 64/66/68 in order to cause fluid to drip from the at least moving belt 36 into the reservoir 42/44/46/88 allowing the dry/empty reservoir(s) 42/44/46/88 to function as a drip tank and a collection reservoir 42/44/46/88.

Additionally, in one arrangement, as one example, the first condition 64, the second condition 66, and/or the third condition 68 facilitates growth of a specific species of microorganism 84. In yet another arrangement, as an example, the first condition 64, the second condition 66, and/or the third condition 68 inhibits growth of a specific type of microorganism 84. In yet another arrangement, as an example, one of the first condition 64, the second condition 66, and/or the third condition 68 facilitates growth of a specific species of microorganism 84 and another inhibits growth of a specific type of microorganism 84.

Motor

Motor 26 is formed of any suitable size, shape, and design. Motor 26 is any form of a motor that converts electrical energy to mechanical energy and provides rotation and torque. In one arrangement, as one example, the motor 26 can include a gear system 30 that is capable of driving the at least one drive shaft 28 wherein the at least one drive shaft 28 rotates the at least one moving belt 36. The rotating of the at least one moving belt 36 allows the at least one moving belt 36 to be in a submerged position 70/72/74 wherein a portion of the at least one moving belt 36 is submerged within the fluid 58/60/62 held within the reservoir 42/44/46/88, and an exposed position 76 wherein a portion of the at least one moving belt 36 is not submerged within the fluid 58/60/62 held within the reservoir 42/44/46/88.

Drive Shaft

The microorganism growing apparatus 12 comprises at least one drive shaft 28 which is formed of any suitable size, shape, and design. In one arrangement, as one example, the at least one drive shaft 28 extends from one side 18 of the microorganism growing apparatus 12 to the opposing side 18 wherein the at least one moving belt 36 is placed over the at least one drive shaft 28 allowing for the at least one drive shaft 28 to rotate and move the at least one moving belt 36 causing the at least one moving belt 36 to move between a submerged position 70/72/74 wherein a portion of the at least one moving belt 36 is submerged within the fluid 58/60/62 held within the reservoir 42/44/46/88, and an exposed position 76 wherein a portion of the at least one moving belt 36 is not submerged within the fluid 58/60/62 held within the reservoir 42/44/46/88.

Gear System

The microorganism growing apparatus 12 comprises a gear system 30, in addition to other components. In one arrangement, as one example, the gear system 30 may be a plurality of gear systems 30. Any number of gear systems 30 may be used without departing from the scope of the disclosure. For example, the microorganism growing apparatus 12 may comprise one, two, three, four, five, six, seven, eight, nine, ten, or more gear systems 30 without departing from the scope of the disclosure. Furthermore, the gear system 30 is formed of any suitable size, shape, and design.

The gear system 30 may be comprised of any form of a gear system 30 including, but not limited to, a pulley system, that is configured to direct power to the microorganism growing apparatus 12. The gear system 30 is configured to drive the at least one drive shaft 28 wherein the at least one drive shaft 28 rotates the at least one moving belt 36. The rotating of the at least one moving belt 36 allows the at least one moving belt 36 to be in a submerged position 70/72/74 wherein a portion of the at least one moving belt 36 is submerged within the fluid 58/60/62 held within the reservoir 42/44/46/88, and an exposed position 76 wherein a portion of the at least one moving belt 36 is not submerged within the fluid 58/60/62 held within the reservoir 42/44/46/88.

Rollers

The microorganism growing apparatus 12 may comprise, in addition to other components, a plurality of rollers 32. The plurality of rollers 32 is formed of any suitable size, shape, and design. In one arrangement, as one example, the plurality of rollers 32 are cylindrical in shape. However, any other shape or configuration is hereby contemplated for use. Additionally, in one arrangement, as an example, one, two, three, four, five, or more rollers 32 may be used. Any number of rollers 32 may be used without departing from the scope of the disclosure.

The plurality of rollers 32 is formed of any suitable size, shape, and design and is configured to provide guidance, direction, and support to the at least one moving belt 36 as the at least one moving belt 36 moves through the microorganism growing apparatus 12.

Pump

The microorganism growing apparatus 12 may comprise, in addition to other components, a pump 82. The pump 82 is formed of any suitable size, shape, and design. Pump 82 may be formed of any size without departing from the disclosure.

Pump 82 is configured to circulate fluid 58 within the first reservoir 42 which may improve the growth of algae 52 and the efficiency of the system 10. Pump 82 can be any type of pump 82 including, but not limited to, an electric pump, a wheel, a paddlewheel or any other type of pump 82 that is configured to circulate fluid 58.

Mechanized Harvesting System

The microorganism growing apparatus 12 may comprise, in addition to other components, a mechanized harvesting system 34. The mechanized harvesting system 34 is formed of any suitable size, shape, and design. The mechanized harvesting system 34 comprises at least one moving belt 36, a harvesting blade 38, and a harvesting reservoir 40. The mechanized harvesting system 34 may be triangular in shape in order to efficiently move the at least one belt 36 through the microorganism growing apparatus 12 wherein the at least moving belt 36 is transitioned between a first submerged position 70, wherein a portion of the at least one moving belt 36 is submerged within the first fluid 58 held within the first reservoir 42, and an exposed position 76, wherein a portion of the at least one moving belt 36 is not submerged within the first fluid 58 held within the first reservoir 42. As a result, the portion of the at least one moving belt 36 that is not submerged within the first fluid 58 held within the first reservoir 42 is exposed to air (a $CO_2$-rich gaseous phase) 48 and light 50 (a "sunlight capture" part of the system 10).

Belt

As provided above, the microorganism growing apparatus 12 may comprise, among other components, a mechanized harvesting system 34. The mechanized harvesting system 34 comprises at least one moving belt 36, among other components. The at least one moving belt 36 is formed of any suitable size, shape, and design. The at least one moving belt 36 may be formed of any material without departing from the scope of the disclosure. The at least one belt 36 may be formed of any type of material, including, but not limited to, plastic, metal, non-metal materials, rubber, polyvinyl chloride (PVC), or any other type of material. Furthermore, the at least one moving belt 36 may be referred to as a belt 36, at least one moving belt 36, at least one belt 36, etc. without departing from the disclosure.

In one arrangement, as one example, the at least one belt 36 is controlled by the motor 26, the gear system 30 and the at least one drive shaft 28 wherein the at least one drive shaft 28 rotates the at least one moving belt 36. The rotation of the at least one moving belt 36 allows the at least one moving belt 36 to move through the microorganism growing apparatus 12 wherein the at least one moving belt 36 is transitioned between a first submerged position 70 wherein a portion of the at least one moving belt 36 is submerged within the first fluid 58 held within the first reservoir 42, and then to an exposed position 76 wherein a portion of the at least one moving belt 36 is not submerged within the first fluid 58 held within the first reservoir 42. In another arrangement, the at least one moving belt 36 moves through the microorganism growing apparatus 12 wherein the at least one moving belt 36 is transitioned between a first submerged position 70 wherein a portion a portion of the at least one moving belt 36 is submerged within the first fluid 58 held within the first reservoir 42, then to an exposed position 76 wherein a portion of the at least one moving belt 36 is not submerged within the first fluid 58 held within the first reservoir 42, then the at least one moving belt 36 moves to a second submerged position 72 wherein a portion of the at least one moving belt 36 is submerged within the second fluid 60 held within the second reservoir 44, then the at least one moving belt 36 moves to a third submerged position 74 wherein a portion of the at least one moving belt 36 is submerged within the third fluid 62 held within the third reservoir 46.

The at least one moving belt 36 may move through the microorganism growing apparatus 12 in any type of configuration or movement without departing from the scope of the disclosure. In one arrangement, as one example, the at least one belt 36 moves through the microorganism growing apparatus 12 in a continuous manner or loop between the first submerged position 70, an exposed position 76, the second submerged position 72, an exposed position 76, and a third submerged position 74. In an alternative arrangement, the at least one belt 36 moves in a serpentine manner between a submerged position 70/72/74 and an exposed position 76. Furthermore, the at least one moving belt 36 may move through the microorganism growing apparatus 12 in any direction or configuration, including, but not limited to, horizontal, vertical, downward, upward, etc. without departing from the scope of the disclosure. In one arrangement, as shown, the at least one moving belt 36 moves through the microorganism growing apparatus 12 in a substantially vertical configuration.

As stated above, the at least one moving belt 36 may comprise any type of microorganism 84 or element without departing from the disclosure. In one embodiment, algae 52 is grown on the at least one moving belt 36. In another arrangement, as one example, algae 52 is grown on the at least one moving belt 36 and the at least one moving belt 36 further comprises bacteria and/or fungi. In an alternative arrangement, the at least one moving belt 36 comprises only one type of microorganism 84 such as algae 52, bacteria, or fungi. However, in another arrangement, the at least one moving belt 36 comprises any combination of varying types of microorganisms 84 such as algae 52, bacteria, or fungi.

Coating

As provided above, the microorganism growing apparatus 12 may comprise, among other components, a mechanized harvesting system 34. The mechanized harvesting system 34 comprises at least one moving belt 36, among other components. The at least one moving belt 36 may comprise a coating on the at least one moving belt 36 that is capable of binding pollutants 56. The coating may be comprised of any type of material, including, but not limited to, coatings that create temporary ionic, covalent, polar, or hydrogen bonds with a pollutant, or any other type of material. In one arrangement, as one example, the at least one moving belt 36 comprises a Lanthanum coating. Furthermore, any amount, volume, or thickness of the coating may be utilized on the at least one moving belt 36 without departing from the disclosure.

In one arrangement, as one example, the at least one moving belt 36 comprises a coating that is capable of binding pollutants 56 as the at least one moving belt 36 cycles through the microorganism growing apparatus 12. In this arrangement, the at least one moving belt 36 moves to a first submerged position 70 wherein a portion of the at least one moving belt 36 is submerged within the first fluid 58 held within the first reservoir 42 exposing the coating to be exposed to the first condition 64 and causing the coating to uptake the pollutants 56; then the at least one moving belt 36 moves to a second submerged position 72 wherein a portion of the at least one moving belt 36 is submerged within the second fluid 60 held within the second reservoir 44 exposing the coating to the second condition 66 and causing the coating to release the pollutants 56.

In one arrangement, as one example, the at least one moving belt 36 comprises microorganisms 84 and a coating. In another arrangement, the at least one moving belt 36 comprises microorganisms 84 and the at least one moving belt 36 does not comprise a coating. Furthermore, in yet another arrangement, the at least one moving belt 36 comprises a coating but the at least one moving belt 36 does not comprise microorganisms 84. For clarification, the at least one moving belt 36 may comprise any combination of microorganisms 84 and/or coating without departing from the disclosure.

Harvesting Blade

As the at least one moving belt 36 moves through the microorganism growing apparatus 12, microorganisms 84 grow on the at least one moving belt 36. The microorganisms 84 that are produced must be harvested or removed from the at least one moving belt 36. The microorganisms 84 may be removed from the at least one moving belt 36 by utilizing any method without departing from the scope of the disclosure. One method of harvesting the microorganisms 84 that are produced is to scrape the microorganisms 84 off of the at least one moving belt 36. In one arrangement, the system 10 comprises the step of harvesting the microorganisms 84 by positioning a harvesting blade 38 along the at least one moving belt 36 in order to scrape the microorganisms 84 off of the at least one moving belt 36. Therefore, the mechanized harvesting system 34 comprises a harvesting blade 38.

In one arrangement, as one example, as the at least one moving belt 36 moves through the microorganism growing apparatus 12, algae 52 grows in a biofilm 54 which forms on the at least one moving belt 36. The algae 52 that is produced must be harvested or removed from the at least one moving belt 36. The algae 52 may be harvested or removed from the at least one moving belt 36 by utilizing any method without departing from the scope of the disclosure. One method of harvesting the algae 52 that is produced is to scrape the algae 52 off of the at least one moving belt 36. In one arrangement, the system 10 comprises the step of harvesting the algae 52 by positioning a harvesting blade 38 along the at least one moving belt 36 in order to scrape the algae 52 off of the at least one moving belt 36.

The harvesting blade 38 is formed of any suitable size, shape, and design. The harvesting blade 38 may be formed of any material that is suitable for harvesting or removing microorganisms 84 from the at least one moving belt 36, such as a squeegee, a piece of plastic, a piece of rubber, a piece of metal, or the like. The harvesting blade 38 may be formed of any material without departing from the scope of the disclosure.

Harvesting Reservoir

As stated above, the microorganism growing apparatus 12 may comprise, in addition to other components, a mechanized harvesting system 34. The mechanized harvesting system 34 may comprise, among other components, a harvesting reservoir 40. The harvesting reservoir 40 may be formed of any suitable size, shape, and design. Furthermore, the harvesting reservoir 40 may be formed of any material that is suitable for accepting and storing microorganisms 84. The harvesting reservoir 40 may be formed of any material without departing from the scope of the disclosure. The harvesting reservoir 40 may be connected to the harvesting blade 38 or positioned next to the harvesting blade 38 and is configured to receive the microorganisms 84 as the microorganisms 84 are harvested from the at least one moving belt 36.

Fluid

As stated above, the microorganism growing apparatus 12 comprises at least one fluid 58/60/62, among other components. The fluid 58/60/62 may be any type of fluid 58/60/62, including, but not limited to, water, wastewater, effluent, and the like. In one arrangement, as one example, the fluid 58/60/62 is effluent from a feed manufacturer which contains a high concentration of pollutants 56 including, but not limited to, N, P, K, C, toxic metals, salts, pharmaceuticals, any type of PPCPs, or hormones. In another arrangement, as one example, the fluid 58/60/62 is municipal water which contains a high concentration of pollutants 56 including, but not limited to, N, P, K, C, toxic metals, salts, pharmaceuticals, any type of PPCPs, or hormones.

In one arrangement, as shown the microorganism growing apparatus 12 comprises a first reservoir 42, among other components, which contains a first fluid 58. In another arrangement, as shown, the microorganism growing apparatus 12 comprises a first reservoir 42 and a second reservoir 44, among other components, wherein the first reservoir 42 contains a first fluid 58 and the second reservoir 44 contains a second fluid 60. In another arrangement, as shown, the microorganism growing apparatus 12 comprises a first reservoir 42, a second reservoir 44, and a third reservoir 46, among other components, wherein the first reservoir 42 contains a first fluid 58, the second reservoir 44 contains a second fluid 60 and the third reservoir 46 contains a third fluid 62. Any number of reservoirs 42/44/46/88 may be utilized by the system 10 without departing from the scope of the disclosure. For example, the microorganism growing apparatus 12 may comprise one, two, three, four, five, six, seven, eight, nine, ten, or more reservoirs 42/44/46/88 without departing from the scope of the disclosure. As a result, any number of fluids 58/60/62 may be utilized by the system 10 without departing from the scope of the disclosure. Throughout the disclosure, reference to a fluid 58/60/62 refers to a first fluid 58, a second fluid 60, or a third fluid 62, unless the disclosure specifically states that it is referring to only a specific fluid 58/60/62.

In one arrangement, as one example, the microorganism growing apparatus 12 comprises a first reservoir 42 and a second reservoir 44 wherein the first reservoir 42 is filled with a first fluid 58 that contains a pollutant 56 and the first fluid 58 is controlled to have a first condition 64. Furthermore, the second reservoir 44 is filled with a second fluid 60 wherein the second fluid 60 is controlled to have a second condition 66. In this arrangement, microorganisms 84 are grown using the microorganism growing apparatus 12 wherein the microorganisms 84 are exposed to the first fluid 58 within the first reservoir 42 wherein the microorganisms 84 are exposed to the first condition 64 and the microorganisms 84 uptake the pollutant 56 from the first fluid 58. Furthermore, the microorganisms 84 are exposed to light 50 and air 48 and then the microorganisms 84 are exposed to the second fluid 60 wherein the microorganisms 84 are exposed to the second condition 66 and the microorganisms 84 are stimulated to release the pollutant 56. In this arrangement, the microorganisms 84 may be comprised of algae 52.

Furthermore, in this arrangement, the algae 52 may grow in an algae biofilm 54 on the at least one moving belt 36 which moves through the microorganism growing apparatus 12.

In another arrangement, as one example, the microorganism growing apparatus 12 comprises a first reservoir 42, a second reservoir 44, and a third reservoir 46 wherein the first reservoir 42 is filled with a first fluid 58 that contains a pollutant 56 and the first fluid 58 is controlled to have a first condition 64. The second reservoir 44 is filled with a second fluid 60 wherein the second fluid 60 is controlled to have a second condition 66. The third reservoir 46 is filled with a third fluid 62 and the third fluid 62 is controlled to have a third condition 68. In this arrangement, microorganisms 84 are grown using the microorganism growing apparatus 12. In this arrangement, the microorganisms 84 are moved such that they are submerged within the first fluid 58 held within the first reservoir 42 exposing the microorganisms 84 to the first condition 64 wherein the microorganisms 84 uptake the pollutant 56 from the first fluid 58 held within the first reservoir 42; then the microorganisms 84 are moved such that it is in an exposed position 76 and it is exposed to air 48 and light 50; following the uptake of the pollutant 56, the microorganisms 84 are moved to a second submerged position 72 within the second fluid 60 held within the second reservoir 44 exposing the microorganisms 84 to the second condition 66 and stimulating the microorganisms 84 to release the pollutant 56. Then the microorganisms 84 are moved to a third submerged position 74 such that the microorganisms 84 are submerged within the third fluid 62 held within the third reservoir 46 exposing the microorganisms 84 to the third condition 68 and stimulating the microorganisms 84 to release the pollutant 56. In this arrangement, the microorganisms 84 may be comprised of algae 52. Furthermore, in this arrangement, the algae 52 may grow in an algae biofilm 54 on the at least one moving belt 36 which moves through the microorganism growing apparatus 12.

In one arrangement, as one example, the motor 26 includes a gear system 30 that is capable of driving the at least one drive shaft 28 wherein the at least one drive shaft 28 rotates the at least one moving belt 36. The rotation of the at least one moving belt 36 allows the at least one moving belt 36 to be in a submerged position 70/72/74 wherein a portion of the at least one moving belt 36 is submerged within a fluid 58/60/62 held within a reservoir 42/44/46. In one arrangement, as one example, microorganisms 84 are produced as the at least one moving belt 36 moves through the microorganism growing apparatus 12.

Conditions

As stated above, the microorganism growing apparatus 12 comprises at least one fluid 58/60/62, among other components, wherein the fluid 58/60/62 is controlled to have a condition 64/66/68. The condition 64/66/68 may be any type of condition 64/66/68 without departing from the scope of the disclosure. For example, the condition 64/66/68 may be an elevated temperature, an elevated temperature compared to another condition 64/66/68 used within the microorganism growing apparatus 12, an elevated temperature within the range of 30-90 degrees Celsius, an illumination, such as artificial lighting (proton energy), using increased light intensity, infrared heat, exposure to a sorbent material (e.g., zeolite, LECA, POLONITE, ROCKFOS, ferric chloride, aluminum sulfate, etc.), exposure to a phosphorous absorbing material, exposure to a fluid with a high concentration of biological oxygen demand, pH adjustment, the second condition is an elevated pH compared to the first condition, adsorbents (e.g., activated carbon, Lanthanum salts, etc.) in the liquid the microorganism is being exposed to, radiation, a salt, an organic chemical, an organic chemical is the second condition and is not present in the first fluid, an inorganic chemical, an antibiotic, antimicrobials, an herbicide (e.g., dicamba, 2,4-dichlorophenoxyacetic acid, atrazine, glyphosate, paraquat, etc.), pesticide, nematicide, insecticide, hormones (e.g., auxin), growth stimulants, or any combination thereof, among other types of conditions 64/66/68 that have an effect on microorganisms 84. In another example, the condition 64/66/68 may include one or more of d-limonene, a phenol, a terpene, a growth regulator, or a combination thereof. The light intensity may be in a range of, for example, 350 $W/m^2$ to 3,500 $W/m^2$, 350 $W/m^2$ to 1,000 $W/m^2$, 1,000 $W/m^2$ to 3,000 $W/m^2$, or 2,000 $W/m^2$ to 3,500 $W/m^2$. The infrared heat may be used to heat the microorganisms to a temperature in a range of 25-60 degrees Celsius, 25-40 degrees Celsius, or 40-60 degrees Celsius. The pH of the liquid the microorganism is being exposed to may be in a range of, for example, of 3-6, 3-5, 4-5, 5-6, 9-12, 9-11, or 10-12. The salt may have a concentration in a range of, for example, 35-350 ppt, 35-150 ppt, or 150-350 ppt.

The condition 64/66/68 may have an effect on microorganisms 84 including, but not limited to, stimulating microorganisms 84 to uptake a pollutant 56, stimulating microorganisms 84 to release a pollutant 56, facilitating growth of microorganisms 84, inhibiting growth of microorganisms 84, or a combination thereof. Inhibiting growth of an undesirable species or consortium can allow more desirable species to grow on the biofilm. The desirable species could grow faster, remove more pollutants or release/uptake pollutants on demand. Inhibiting growth of an undesirable species or consortium can may occur where the microorganisms release or contain toxins. Inhibiting growth of an undesirable species or consortium can may occur where the microorganisms do not have a desirable composition. For example, one condition may result in uptaking the pollutant 56 and either facilitating or inhibiting the growth of the microorganisms 84. In another example, one condition may result in stimulating the microorganisms 84 to release the pollutant 56 and either facilitating or inhibiting the growth of the microorganisms 84. In another example, one condition may result in facilitating the growth of one type of microorganism while inhibiting the growth of another type of microorganism. In another example, one condition may result in facilitating the growth of one type of microorganism while another condition results in inhibiting the growth of another type of microorganism.

The system 10 may comprise any number of reservoirs 42/44/46/88, fluids 58/60/62, and conditions 64/66/68 without departing from the scope of the disclosure. Therefore, the system 10 may comprise one, two, three, four, five, six, seven, eight, nine, ten, or more reservoirs 42/44/46/88, fluids 58/60/62, and conditions 64/66/68 without departing from the scope of the disclosure.

In one arrangement, as one example, the microorganism growing apparatus 12 comprises a first reservoir 42 and a second reservoir 44 wherein the first reservoir 42 is filled with a first fluid 58 and the first fluid 58 is controlled to have a first condition 64 and the second reservoir 44 is filled with a second fluid 60 and the second fluid 60 is controlled to have a second condition 66. In another arrangement, as one example, the microorganism growing apparatus 12 comprises a first reservoir 42, a second reservoir 44, and a third reservoir 46 wherein the first reservoir 42 is filled with a first fluid 58 and the first fluid 58 is controlled to have a first condition 64, the second reservoir 44 is filled with a second fluid 60 and the second fluid 60 is controlled to have a second condition 66, and the third reservoir 46 is filled with a third fluid 62 and the third fluid 62 is controlled to have a third condition 68.

Any number of reservoirs 42/44/46/88 may be utilized by the system 10 without departing from the scope of the disclosure. For example, the microorganism growing apparatus 12 may comprise one, two, three, four, five, six, seven, eight, nine, ten, or more reservoirs 42/44/46/88 without departing from the scope of the disclosure. As a result, any number of fluids 58/60/62 and conditions 64/66/68 may be utilized by the system 10 without departing from the scope of the disclosure. Throughout the disclosure, reference to a condition 64/66/68 refers to a first condition 64, a second condition 66, or a third condition 68, unless the disclosure specifically states that it is referring to only a specific condition 64/66/68.

In one arrangement, as shown the microorganism growing apparatus 12 comprises a first reservoir 42, among other components, which contains a first fluid 58 wherein the first fluid 58 is controlled to have a first condition 64. In another arrangement, as shown, the microorganism growing apparatus 12 comprises a first reservoir 42 and a second reservoir 44, among other components, wherein the first reservoir 42 contains a first fluid 58 and the second reservoir 44 contains a second fluid 60 wherein the first fluid 58 is controlled to have a first condition 64 and the second fluid 60 is controlled to have a second condition 66. In another arrangement, as shown, the microorganism growing apparatus 12 comprises a first reservoir 42, a second reservoir 44, and a third reservoir 46, among other components, wherein the first reservoir 42 contains a first fluid 58 and the first fluid 58 is controlled to have a first condition 64, the second reservoir 44 contains a second fluid 60 and the second fluid 60 is controlled to have a second condition 66, and the third reservoir 46 contains a third fluid 62 and the third fluid 62 is controlled to have a third condition 68.

In one arrangement, as one example, the microorganism growing apparatus 12 comprises a first reservoir 42 and a second reservoir 44 wherein the first reservoir 42 is filled with a first fluid 58 that contains a pollutant 56 and the first fluid 58 is controlled to have a first condition 64. Furthermore, the second reservoir 44 is filled with a second fluid 60 wherein the second fluid is controlled to have a second condition 66. In this arrangement, microorganisms 84 are grown using the microorganism growing apparatus 12 wherein the microorganisms 84 are exposed to the first fluid 58 within the first reservoir 42 wherein the microorganisms 84 are exposed to the first condition 64 and the microorganisms 84 uptake the pollutant 56 from the first fluid 58. Furthermore, the microorganisms 84 are exposed to light 50 and air 48 and then the microorganisms 84 are exposed to the second fluid 60 wherein the microorganisms 84 are exposed to the second condition 66 and the microorganisms 84 are stimulated to release the pollutant 56. In this arrangement, the microorganisms 84 may be comprised of algae 52. Furthermore, in this arrangement, the algae 52 may grow in an algae biofilm 54.

In another arrangement, as one example, the microorganism growing apparatus 12 comprises a first reservoir 42, a second reservoir 44, and a third reservoir 46 wherein the first reservoir 42 is filled with a first fluid 58 that contains a pollutant 56 and the first fluid 58 is controlled to have a first condition 64. The second reservoir 44 is filled with a second fluid 60 wherein the second fluid 60 is controlled to have a second condition 66. The third reservoir 46 is filled with a third fluid 62 and the third fluid 62 is controlled to have a third condition 68. In this arrangement, microorganisms 84 are grown using the microorganism growing apparatus 12. In this arrangement, the microorganisms 84 are moved to a first submerged position 70 such that the microorganisms 84 are submerged within the first fluid 58 held within the first reservoir 42 exposing the microorganisms 84 to the first condition 64 wherein the microorganisms 84 uptake the pollutant 56 from the first fluid 58 held within the first reservoir 42; then the microorganisms 84 are moved such that it is in an exposed position 76 and it is exposed to air 48 and light 50; following the uptake of the pollutant 56, the microorganisms 84 are moved to a second submerged position 72 within the second fluid 60 held within the second reservoir 44 exposing the microorganisms 84 to the second condition 66 and stimulating the microorganisms 84 to release the pollutant 56. Then the microorganisms 84 are moved to a third submerged position 74 such that the microorganisms 84 are submerged within the third fluid 62 held within the third reservoir 46 exposing the microorganisms 84 to the third condition 68 and stimulating the microorganisms 84 to release the pollutant 56. In this arrangement, the microorganisms 84 may be comprised of algae 52. Furthermore, in this arrangement, the algae 52 may grow in an algae biofilm 54.

In one arrangement, as an example, the first condition 64, the second condition 66, and/or the third condition 68 facilitates growth of a specific type of microorganism 84. In one arrangement, the first condition 64, the second condition 66, and/or the third condition 68 inhibits growth of a specific type of microorganism 84.

In one arrangement, as one example, the motor 26 includes a gear system 30 that is capable of driving the at least one drive shaft 28 wherein the at least one drive shaft 28 rotates the at least one moving belt 36. The rotation of the at least one moving belt 36 allows the at least one moving belt 36 to be in a submerged position 70/72/74 wherein a portion of the at least one moving belt 36 is submerged within the fluid 58/60/62 held within the reservoir 42/44/46/88. In one arrangement, as one example, microorganisms 84 are produced as the at least one moving belt 36 moves through the microorganism growing apparatus 12.

In Operation

In one arrangement, as one example, the system 10 comprises the steps of: providing a microorganism growing apparatus 12 having a first reservoir 42 and a second reservoir 44, filling the first reservoir 42 with a first fluid 58 that contains a pollutant 56, controlling the first fluid 58 within the first reservoir 42 to have a first condition 64, filling the second reservoir 44 with a second fluid 60, controlling the second fluid 60 within the second reservoir 44 to have a second condition 66, growing microorganisms 84 using the microorganism growing apparatus 12, exposing the microorganisms 84 to light 50 and air 48, and exposing the microorganisms 84 to the second fluid 60 within the second reservoir 44 wherein the microorganisms 84 are exposed to the second condition 66 and the microorganisms 84 are stimulated to release the pollutant 56. In one arrangement, the system 10 further comprises the step of: following release of the pollutant 56, the microorganisms 84 are then brought back to the first reservoir 42 to uptake additional pollutants 56 and the process is repeated. Furthermore, in one arrangement, as one example, the system 10 further comprises the step of: starving the microorganisms 84 of the pollutant 56 by exposing the microorganisms 84 to the second condition 66 thereby causing the microorganisms 84 to consume increased amounts of the pollutant 56 from the first fluid 58 in the first reservoir 42. In one arrangement, as one example, the system 10 comprises concentrating the pollutant 56 within the second fluid 60 held within the second reservoir 44. In one example, the system 10 grows the microorganisms 84 on a belt 36 wherein the belt 36 moves in a continuous manner through the reservoirs 42/44/46.

Furthermore, in one arrangement, as one example, the system 10 may further comprise the steps of: providing a third reservoir 46, filling the third reservoir 46 with a third fluid 62, controlling the third fluid 62 within the third reservoir 46 to have a third condition 68, and submerging a portion of the belt 36 containing the microorganisms 84 within the third fluid 62 of the third reservoir 46 thereby exposing this portion of the microorganisms 84 to the third condition 68.

In one example, the system 10 further comprises the step of controlling the temperature of the air 48 within the microorganism growing apparatus 12, controlling the temperature of the second fluid 60 within the second reservoir 44, and/or controlling the light 50 within the microorganism growing apparatus 12 in order to facilitate growth of the microorganisms 84. Additionally, in one arrangement, as one example, the system 10 further comprises the step of harvesting the microorganisms 84 and using the harvested microorganisms 84 as a foodstuff for human or non-human animal consumption, a fertilizer, a bioplastic, and/or a biofuel.

In another arrangement, as one example, the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; filling the second reservoir 44 with a second fluid 60; controlling the second fluid 60 within the second reservoir 44 to have a second condition 66; growing microorganisms 84 using the microorganism growing apparatus 12; moving the microorganisms 84 such that a portion of the microorganisms 84 are submerged within the first fluid 58 held within the first reservoir 42 exposing the microorganisms 84 to the first condition 64 wherein the microorganisms 84 uptake the pollutant 56 from the first fluid 58 held within the first reservoir 42; moving the microorganisms 84 such that a portion of the microorganisms 84 are exposed to air 48 and light 50; and following the uptake of the pollutant 56, moving the microorganisms 84 such that a portion of the microorganisms 84 are submerged within the second fluid 60 held within the second reservoir 44 exposing the microorganisms 84 to the second condition 66 and stimulating the microorganisms 84 to release the pollutant 56. In one arrangement, the system 10 further comprises the step of: following release of the pollutant 56, the microorganisms 84 are then brought back to the first reservoir 42 to uptake additional pollutants 56 and the process is repeated. Furthermore, in one arrangement, as one example, the system 10 further comprises the step of: starving the microorganisms 84 of the pollutant 56 by exposing the microorganisms 84 to the second condition 66 thereby causing the microorganisms 84 to consume increased amounts of the pollutant 56 from the first fluid 58 in the first reservoir 42. In one arrangement, as one example, the system 10 comprises concentrating the pollutant 56 within the second fluid 60 held within the second reservoir 44. In one example, the system 10 grows the microorganisms 84 on a belt 36 wherein the belt 36 moves in a continuous manner through the reservoirs 42/44/46.

In one example, the system 10 further comprises the step of controlling the temperature of the air 48 within the microorganism growing apparatus 12, controlling the temperature of the second fluid 60 within the second reservoir 44, and/or controlling the light 50 within the microorganism growing apparatus 12 in order to facilitate growth of the microorganisms 84. Additionally, in one arrangement, as one example, the system 10 further comprises the step of harvesting the microorganisms 84 and using the harvested microorganisms 84 as a foodstuff for human or non-human animal consumption.

Furthermore, in one arrangement, as one example, the system 10 may further comprise the steps of: providing a third reservoir 46, filling the third reservoir 46 with a third fluid 62, controlling the third fluid 62 within the third reservoir 46 to have a third condition 68, and submerging a portion of the microorganisms 84 within the third fluid 62 of the third reservoir 46 thereby exposing this portion of the microorganisms 84 to the third condition 68.

Also, in one arrangement, as an example, the first condition 64, the second condition 66, and/or the third condition 68 facilitates growth of a specific species of microorganism 84. In one arrangement, the first condition 64, the second condition 66, and/or the third condition 68 inhibits growth of a specific type of microorganism 84.

System 10 Comprising at Least One Belt 36 in Operation:

In another arrangement, as one example, the system 10 comprises the steps of: providing a microorganism growing apparatus 12 having a first reservoir 42, a second reservoir 44, and at least one moving belt 36; filling the first reservoir 42 with a first fluid 58 that has a high concentration of the pollutant 56; controlling the first fluid 58 within the first reservoir 42 to have a first condition 64; filling the second reservoir 44 with a second fluid 60; controlling the second fluid 60 within the second reservoir 44 to have a second condition 66; moving the at least one belt 36 between a first submerged position 70, wherein a portion of the at least one belt 36 is submerged within the first fluid 58 held within the first reservoir 42, and an exposed position 76, wherein a portion of the at least one belt 36 is not submerged within the first fluid 58 held within the first reservoir 42; exposing the portion of the at least one belt 36 in the exposed position 76 to air 48 and light 50; growing microorganisms 84 on the at least one belt 36 as the at least one belt 36 moves through the microorganism growing apparatus 12, wherein the microorganisms 84 consume the pollutant 56 from the first fluid 58 held within the first reservoir 42 during the growing process; submerging a portion of the at least one belt 36 within the second fluid 60 of the second reservoir 44 thereby exposing this portion of the at least one belt 36 to the second condition 66 thereby stimulating the microorganisms 84 contained on this portion of the belt 36 to release the pollutant 56. In one arrangement, the system 10 further comprises the step of: following release of the pollutant 56, the microorganisms 84 are then brought back to the first reservoir 42 to uptake additional pollutants 56 and the process is repeated. Furthermore, in one arrangement, as one example, the system 10 further comprises the step of: starving the microorganisms 84 of the pollutant 56 by exposing the microorganisms 84 to the second condition 66 thereby causing the microorganisms 84 to consume increased amounts of the pollutant 56 from the first fluid 58 in the first reservoir 42. In one arrangement, as one example, the system 10 comprises concentrating the pollutant 56 within the second fluid 60 held within the second reservoir 44. In one example, the system 10 grows the microorganisms 84 on a belt 36 wherein the belt 36 moves in a continuous manner through the reservoirs 42/44/46. Furthermore, in one arrangement, the belt 36 moves in a continuous loop between the first submerged position 70 and the second submerged position 72. In another arrangement, the belt 36 moves in a serpentine manner between the first submerged position 70 and the second submerged position 72. In one arrangement, the at least one belt 36 moves in a serpentine manner in a generally vertical manner thereby reducing the footprint of the microorganism growing apparatus 12. Additionally, in one arrangement, the at least one belt 36 continuously passes through the second reservoir 44. In another arrangement, the at least one belt 36 only periodically passes through the second reservoir 44.

In one example, the system 10 further comprises the step of controlling the temperature of the air 48 within the microorganism growing apparatus 12, controlling the temperature of the second fluid 60 within the second reservoir 44, and/or controlling the light 50 within the microorganism growing apparatus 12 in order to facilitate growth of the microorganisms 84. Additionally, in one arrangement, as one example, the system 10 further comprises the step of harvesting the microorganisms 84 and using the harvested microorganisms 84 as a foodstuff for human or non-human animal consumption, a fertilizer, a bioplastic, and/or a biofuel.

In one arrangement, as one example, the system 10 may further comprise the steps of: providing a third reservoir 46, filling the third reservoir 46 with a third fluid 62, controlling the third fluid 62 within the third reservoir 46 to have a third condition 68, and submerging a portion of the microorganisms 84 within the third fluid 62 of the third reservoir 46 thereby exposing this portion of the microorganisms 84 to the third condition 68.

Furthermore, in one arrangement, as an example, the system 10 further comprises the step of harvesting the microorganisms 84 by scraping a blade 38 along the at least one belt 36. Also, in one arrangement, the system 10 further comprises the step of harvesting the microorganisms 84 and using the harvested microorganisms 84 as a foodstuff for human or non-human animal consumption.

In an alternative arrangement, the system 10 comprises the steps of: providing a microorganism growing apparatus 12 having a first reservoir 42 and a second reservoir 44; filling the first reservoir 42 with a first fluid 58 that contains a pollutant 56; controlling the first fluid 58 within the first reservoir 42 to have a first condition 64; allowing the second reservoir 44 to be dry/empty by not filling the second reservoir 44 with a fluid or by draining the second reservoir 44 of the fluid contained therein; controlling the second reservoir 44 to have a second condition 66; growing microorganisms 84 using the microorganism growing apparatus 12; exposing the microorganisms 84 to the first fluid 58 within the first reservoir 42 wherein the microorganisms 84 are exposed to the first condition 64 and the microorganisms 84 uptake the pollutant 56 from the first fluid 58; exposing the microorganisms 84 to light 50 and air 48; and exposing the microorganisms 84 to the second reservoir 44 wherein the microorganisms 84 are exposed to the second condition 66 and the microorganisms 84 are stimulated to release the pollutant 56. This arrangement of the system 10 may also comprise the steps of: providing a third reservoir 46 wherein the third reservoir 46 may be filled with a fluid 62 and the fluid 62 is controlled to have a third condition 68 and a portion of the microorganisms 84 are submerged within the fluid 62 of the third reservoir 46 thereby exposing this portion of the microorganisms 84 to the third condition 68.

In one arrangement, as an example, the first condition 64, the second condition 66, and/or the third condition 68 facilitates growth of a specific species of microorganism 84.

In one arrangement, the first condition 64, the second condition 66, and/or the third condition 68 inhibits growth of a specific type of microorganism 84.

Additionally, the system 10 may comprise any configuration without departing from the disclosure including, but not limited to, any configuration wherein microorganisms 84 are circulated throughout reservoirs 42/44/46/88 in order to be exposed to fluids 58/60/62 and conditions 64/66/68 contained therein in order to uptake and release a pollutant 56. Thus, in one arrangement, the system 10 comprises a first reservoir 42 filled with a first fluid 58 and a second reservoir 44 filled with a second fluid 60. In another arrangement, the system 10 comprises a first reservoir 42 filled with a first fluid 58, a second reservoir 44 which is dry/empty, and a third reservoir 46 which is filled with a fluid 62. In yet another arrangement, the system 10 comprises a first reservoir 42 filled with a first fluid 58, a second reservoir 44 filled with a second fluid 60, and a third reservoir 46 which is dry/empty. In an alternative arrangement, the system 10 comprises a first reservoir 42 which is filled with a first fluid 58, a second reservoir 44 which is dry/empty, a third reservoir 46 which is filled with a fluid 62, and a fourth reservoir 88 which is dry/empty. In yet another alternative configuration, the system 10 comprises a first reservoir 42 which is filled with a first fluid 58 and a second reservoir 44 which is dry/empty and functions as a drip tank.

Benefits of System

The system 10 has many benefits and advantages including, but not limited to, providing a method of using microorganisms 84 to remove a pollutant 56 from a fluid 58 that is efficient; providing a method of using microorganisms 84 to remove a pollutant 56 from a fluid 58 that is simple in design; providing a method of using microorganisms 84 to remove a pollutant 56 from a fluid 58 that is inexpensive; providing a method of using microorganisms 84 to remove a pollutant 56 from a fluid 58, harvesting the microorganisms 84, and using the microorganisms 84 as a foodstuff for human consumption; providing a method of using microorganisms 84 to remove a pollutant 56 from a fluid 58, harvesting the microorganisms 84, and using the microorganisms 84 as a foodstuff for animal consumption; providing a method of using microorganisms 84 to remove a pollutant 56 from a fluid 58 that is capable of meeting current pollutant 56 discharge limits; providing a method of using microorganisms 84 to remove a pollutant 56 from a fluid 58 that has a smaller footprint than other biological systems; providing a method of using microorganisms 84 to efficiently and effectively remove a pollutant 56 from effluent; providing a method of using microorganisms 84 to remove a pollutant 56 from a fluid 58 that has a high pollutant 56 removal rate; providing a method of facilitating growth of specific microorganisms; providing a method of inhibiting growth of specific microorganisms. These and other benefits and advantages of the system 10 are apparent from the specification and claims.

In various embodiments disclosed herein, a single component can be replaced by multiple components and multiple components can be replaced by a single component to perform a given function or functions. Except where such substitution would not be operative, such substitution is within the intended scope of the embodiments.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A method of facilitating or inhibiting growth of a species or consortium of microorganisms, the method comprising:
   providing a growing apparatus having a first reservoir containing a first fluid, and a second reservoir containing a second fluid, and at least one moving belt operably configured to directly travel through both the first fluid and the second fluid;
   growing microorganisms using the growing apparatus;
   exposing the microorganisms to the first fluid within the first reservoir, wherein the microorganisms are exposed to a first condition;
   exposing the microorganisms to light and air outside of the first reservoir; and
   exposing the microorganisms to the second fluid, wherein the microorganisms are exposed to a second condition;
   wherein one or more of the first condition or the second condition:
      facilitates growth of a desirable species or consortium of microorganisms, or
      inhibits growth of an undesirable species or consortium of microorganisms.

2. The method of claim 1, wherein the first fluid contains a pollutant, the first condition stimulates the microorganisms to uptake the pollutant from the first fluid, and the second condition stimulates the microorganisms to release the pollutant.

3. The method of claim 1, further comprising, after exposing the microorganisms to the second fluid, exposing the microorganisms to the first fluid again.

4. The method of claim 1, wherein the at least one moving belt comprises a coating.

5. The method of claim 1, wherein the at least one moving belt moves in a continuous manner.

6. The method of claim 1, wherein the microorganisms are algae, bacteria, fungi, or a combination thereof.

7. The method of claim 1, wherein the second condition is an elevated temperature compared to the first condition.

8. The method of claim 1, wherein the second condition is an elevated temperature within a range of 30-90 degrees Celsius.

9. The method of claim 1, wherein the second condition is an illumination using increased light intensity.

10. The method of claim 1, wherein the second condition is exposure to a sorbent material.

11. The method of claim 1, wherein the second condition is radiation.

12. The method of claim 1, wherein the second condition is an elevated pH compared to the first condition.

13. The method of claim 1, wherein the second condition is a salt.

14. The method of claim 1, wherein the second condition is an organic chemical.

15. The method of claim 14, wherein the organic chemical is not present in the first fluid.

16. The method of claim 1, wherein the second condition is an inorganic chemical.

17. The method of claim 1, wherein the second condition includes hormones.

18. The method of claim 1, wherein the second condition includes growth stimulants.

19. The method of claim 1, wherein the second condition includes antimicrobials.

20. The method of claim 1, further comprising harvesting the microorganisms.

21. The method of claim 1, wherein the growing apparatus further comprises a third reservoir containing a third fluid, the method further comprising:
   exposing the microorganisms to the third fluid, wherein the microorganisms are exposed to a third condition,
   wherein one or more of the first condition, the second condition, or the third condition:
      facilitates growth of the desirable species or consortium of microorganisms, or
      inhibits growth of the undesirable species or consortium of microorganisms.

* * * * *